(12) United States Patent
Rickman

(10) Patent No.: US 10,632,236 B2
(45) Date of Patent: Apr. 28, 2020

(54) INCONTINENCE AID

(71) Applicant: James Rickman, Paducah, KY (US)

(72) Inventor: James Rickman, Paducah, KY (US)

( * ) Notice: Subject to any disclaimer, the term of this patent is extended or adjusted under 35 U.S.C. 154(b) by 0 days.

(21) Appl. No.: 16/368,348

(22) Filed: Mar. 28, 2019

(65) Prior Publication Data

US 2019/0216992 A1    Jul. 18, 2019

Related U.S. Application Data

(63) Continuation of application No. 15/715,913, filed on Sep. 26, 2017, now Pat. No. 10,335,523, which is a continuation-in-part of application No. 35/001,114, filed on Nov. 19, 2015 (U.S. filing date under 35 U.S.C. 384), and having an international filing date of Nov. 19, 2015, now Pat. No. Des. 806,871.

(60) Provisional application No. 62/402,664, filed on Sep. 30, 2016.

(51) Int. Cl.
| | |
|---|---|
| *A61F 13/471* | (2006.01) |
| *A61M 1/00* | (2006.01) |
| *A61F 13/47* | (2006.01) |
| *A61F 13/472* | (2006.01) |
| *A61F 5/451* | (2006.01) |
| *A61F 13/475* | (2006.01) |
| *A61F 13/84* | (2006.01) |
| *A61F 13/476* | (2006.01) |
| *A61F 13/45* | (2006.01) |

(52) U.S. Cl.
CPC .......... *A61M 1/0088* (2013.01); *A61F 5/451* (2013.01); *A61F 13/471* (2013.01); *A61F 13/472* (2013.01); *A61F 13/4704* (2013.01); *A61F 13/476* (2013.01); *A61F 13/4756* (2013.01); *A61F 13/84* (2013.01); *A61F 2013/4506* (2013.01); *A61F 2013/4562* (2013.01); *A61M 2205/0216* (2013.01)

(58) Field of Classification Search
CPC . A61M 1/0088; A61F 13/4704; A61F 13/471; A61F 13/472; A61F 13/4756; A61F 13/476; A61F 13/84; A61F 5/451; A61F 5/453
See application file for complete search history.

(56) References Cited

U.S. PATENT DOCUMENTS

| | | | |
|---|---|---|---|
| 3,858,584 | A | 1/1975 | Johnson |
| 4,576,599 | A | 3/1986 | Lipner |
| 4,627,846 | A | 12/1986 | Ternstrom |
| 5,074,853 | A | 12/1991 | Bryant |
| 5,263,947 | A * | 11/1993 | Kay ............... A61F 5/451 600/574 |
| 5,810,799 | A | 9/1998 | Slater |
| 6,307,118 | B1 | 10/2001 | Reich |
| 6,336,919 | B1 | 1/2002 | Davis et al. |
| 6,371,950 | B1 | 4/2002 | Rolansky et al. |
| 6,479,726 | B1 | 11/2002 | Cole |

(Continued)

*Primary Examiner* — Ariana Zimbouski
(74) *Attorney, Agent, or Firm* — Patterson Intellectual Property Law, P.C.; Seth R. Ogden

(57) ABSTRACT

An incontinence aid may include a pad body. The pad body may include a liquid receiving area. The incontinence aid may further include a liquid passage connected to the pad body. The liquid passage may form a boundary about a majority of the liquid receiving area. The liquid passage may include at least one lateral opening facing the liquid receiving area.

12 Claims, 30 Drawing Sheets

(56) References Cited

U.S. PATENT DOCUMENTS

| | | |
|---|---|---|
| 6,817,992 B1 | 11/2004 | Sassak et al. |
| 7,553,300 B2 | 6/2009 | Elfstrom et al. |
| 8,052,663 B2 | 11/2011 | Harsjo |
| 8,142,409 B2 | 3/2012 | Reddy |
| 8,702,667 B1 | 4/2014 | Johnson |
| 8,702,673 B1 | 4/2014 | Jones |
| 8,926,578 B2 | 1/2015 | Drevik |
| 2002/0099352 A1 | 7/2002 | Heden |
| 2002/0123730 A1 | 9/2002 | Popp et al. |
| 2003/0009144 A1 | 1/2003 | Tanzer et al. |
| 2006/0149196 A1 | 7/2006 | Bjornbereg et al. |
| 2009/0069765 A1 | 3/2009 | Wortham |
| 2010/0125260 A1* | 5/2010 | White .................. A61F 13/471 604/356 |
| 2015/0053210 A1 | 2/2015 | Mathison |
| 2015/0126951 A1* | 5/2015 | Sharkey ................ A61F 13/471 604/385.03 |
| 2015/0128961 A1* | 5/2015 | Zilm .................. A61F 13/4702 128/885 |
| 2016/0008188 A1 | 1/2016 | Lumaque-Steeman |

\* cited by examiner

INCONTINENCE AID

BACKGROUND

The present disclosure relates generally to an incontinence aid. More particularly, the present disclosure pertains to incontinence aids designed for men and women respectively.

An estimated 25% of women over the age of 35 experience some level of urinary incontinence. Childbirth and menopause can potentially increase a woman's likelihood of urinary incontinence.

Men also experience urinary incontinence, albeit at a lower rate. An estimated 10% of men suffer from some level of urinary incontinence. Prostate issues can often be to blame for male urinary incontinence.

As life expectancy of the average person increases, the demand for incontinence products similarly increases. Urinary incontinence becomes increasingly likely with age, particularly in individuals aged 65 or older. Indeed, the global products market for disposable incontinence products was over $8 billion in 2015. This figure is expected to grow beyond $12 billion by 2024.

Many urinary incontinence products are bulky and prevent a user from wearing certain clothing. Some urinary incontinence products may suffer from insufficient leakage protection, thereby preventing a user from enjoying a fully active life without the fear of having an accident in public.

What is needed, therefore, is an improved incontinence aid according to the present disclosure that may address one or more of the above issues.

BRIEF SUMMARY

Briefly, the present disclosure relates, in one embodiment, to an incontinence aid. The incontinence aid may include a pad body. The pad body may include a liquid receiving area. The incontinence aid may further include a liquid passage connected to the pad body. The liquid passage may form a boundary about a majority of the liquid receiving area. The liquid passage may include at least one lateral opening facing the liquid receiving area.

The liquid passage may form a boundary about the entire liquid receiving area.

The incontinence aid may further include a drain connected to the pad body. The drain may be able to receive liquid from at least one of the liquid receiving area and the liquid passage.

The incontinence aid may further include a liquid retention vessel remote from the pad body. The liquid retention vessel may be in fluid communication with the drain.

The drain may be connected to the liquid receiving area of the pad body.

The liquid passage may further include a first liquid passage open end and a second liquid passage open end. The drain may be connected to the pad body between the first liquid passage open end and the second liquid passage open end.

The liquid receiving area may include a liquid collection reservoir defined in the pad body.

The liquid collection reservoir may include a generally oval shape.

The liquid collection reservoir may include a first thickness of the pad body. Other portions of the pad body may include a second thickness of the pad body. The second thickness may be greater than the first thickness.

The pad body may further include at least one ridge. The at least one ridge may be able to direct liquid to the liquid collection reservoir. The at least one ridge may include a third thickness of the pad body. The third thickness may be greater than the first thickness and the second thickness.

The pad body may include a generally hourglass shape.

The liquid passage may include a water-resistant material.

The liquid passage may include a water-proof material.

The pad body may further include a front portion having a front portion width. The pad body may also further include a back portion opposite the front portion. The back portion may have a back portion width. The pad body may further still include a middle portion disposed between the front portion and the back portion. The middle portion may have a middle portion width. The middle portion width may be less than the front portion width and the back portion width.

The front portion width may be greater than the back portion width.

The present disclosure also relates, in one embodiment, to an incontinence aid for men. The incontinence aid may include a pad body. The pad body may include an interior side, an exterior side opposite the interior side, a proximal end, and a distal end opposite the proximal end. The incontinence aid may further include a first fastener permanently connected to the pad body adjacent the proximal end of the pad body. The first fastener may be able to removably attach a first overlapping portion of the pad body adjacent the proximal end of the pad body to the exterior side of the pad body adjacent the proximal end of the pad body. The incontinence aid may also include a second fastener permanently connected to the pad body nearer the distal end of the pad body than the first fastener. The second fastener may be able to removably attach a second overlapping portion of the pad body adjacent the distal end of the pad body to the exterior side of the pad body.

At least a portion of the proximal end of the pad body may be elastic.

The incontinence aid may further include an elastic band connected to the pad body adjacent the proximal end of the pad body.

The proximal end of the pad body may include a proximal end width. The distal end of the pad body may include a distal end width. The distal end width may be greater than the proximal end width.

The present disclosure also relates, in an embodiment, to a method of attaching an incontinence aid to a man. The method may include positioning a pad body of the incontinence aid such that an interior side of the pad body adjacent a proximal end of the pad body is under the man's genitals; folding a first side edge of the pad body over at least a portion of the man's genitals such that the interior side of the pad body adjacent the proximal end of the pad body and adjacent the first side edge of the pad body faces at least a portion of the man's genitals; folding a second side edge of the pad body over the first side edge of the pad body such that the interior side of the pad body adjacent the proximal end of the pad body and adjacent the second side edge of the pad body faces at least a portion of an exterior side of the pad body adjacent the proximal end of the pad body and adjacent the first side edge of the pad body; folding the pad body such that the interior side of the pad body adjacent a distal end of the pad body faces at least a portion of the exterior side of the pad body to cover the man's genitals; and securing the pad body in a folded position to retain the pad body on the man's genitals.

The method may further include fastening the interior side of the pad body adjacent the proximal end of the pad body and adjacent the second side edge of the pad body to the exterior side of the pad body adjacent the proximal end of the pad body and adjacent the first side edge of the pad body.

The method may also include fastening the interior side of the pad body adjacent the distal end of the pad body to the exterior side of the pad body.

DETAILED DESCRIPTION

Reference will now be made in detail to embodiments of the present disclosure, one or more drawings of which are set forth herein. Each drawing is provided by way of explanation of the present disclosure and is not a limitation. In fact, it will be apparent to those skilled in the art that various modifications and variations can be made to the teachings of the present disclosure without departing from the scope of the disclosure. For instance, features illustrated or described as part of one embodiment can be used with another embodiment to yield a still further embodiment.

Thus, it is intended that the present disclosure covers such modifications and variations as come within the scope of the appended claims and their equivalents. Other objects, features, and aspects of the present disclosure are disclosed in, or are obvious from, the following detailed description. It is to be understood by one of ordinary skill in the art that the present discussion is a description of exemplary embodiments only and is not intended as limiting the broader aspects of the present disclosure.

The words "connected", "attached", "joined", "mounted", "fastened", and the like should be interpreted to mean any manner of joining two objects including, but not limited to, the use of any fasteners such as one or more sections of hooks and corresponding one or more sections of loops, one or more adhesive strips with optional corresponding attachment surfaces, ribbons, laces, ropes, buttons, and the like allowing for a stationary, translatable, or pivotable relationship; welding of any kind such as friction welding, ultrasonic welding, heat welding, and the like; using any resin, glue, epoxy, and the like; being integrally formed as a single part together; any mechanical fit such as a friction fit, interference fit, slidable fit, rotatable fit, pivotable fit, and the like; any combination thereof; and the like.

Unless specifically stated otherwise, any part of the apparatus of the present disclosure may be made of any appropriate or suitable material.

Figure 1:
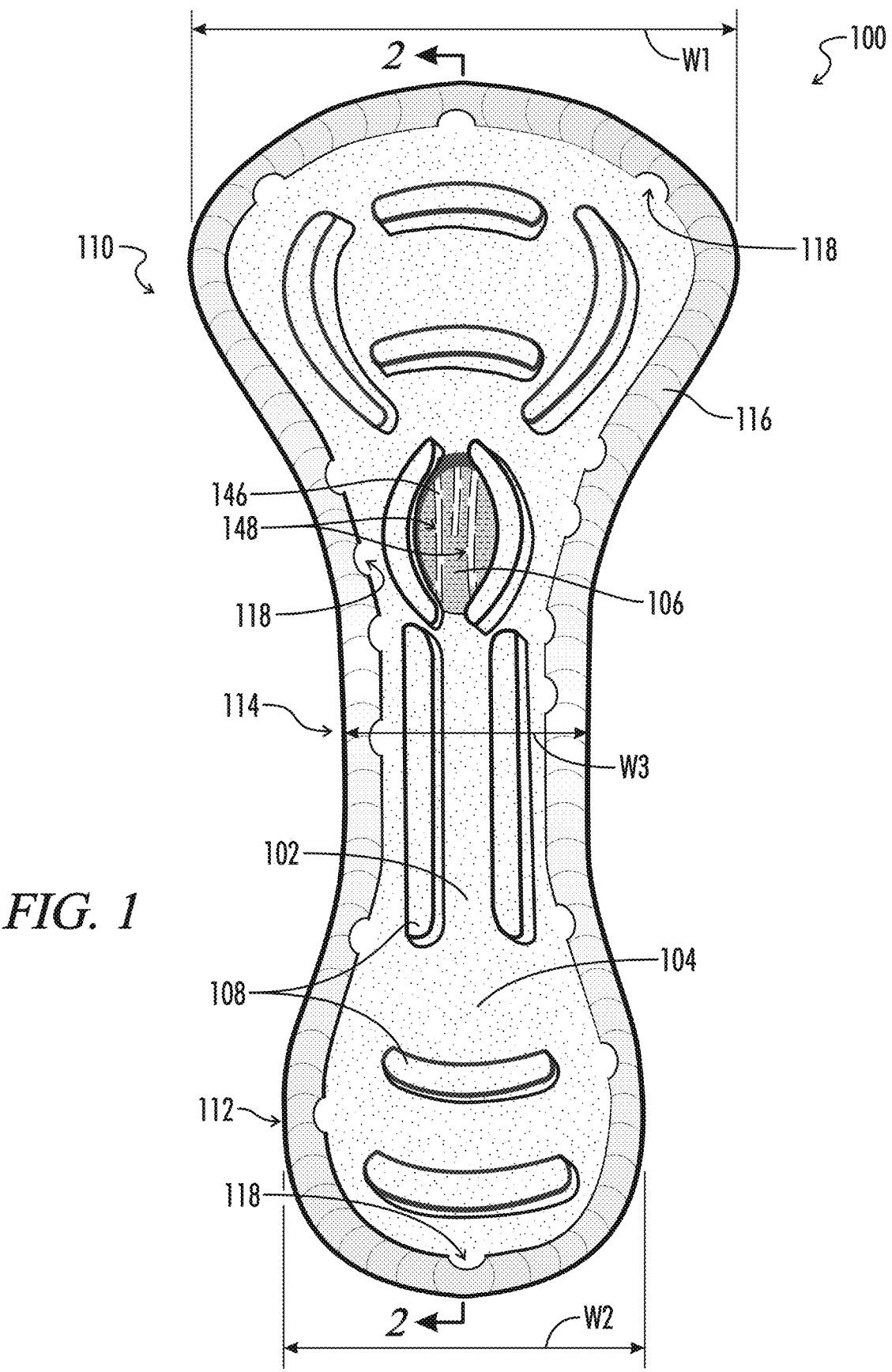
FIG. 1 is a front elevation view of an embodiment of an incontinence aid.
Figure 2:
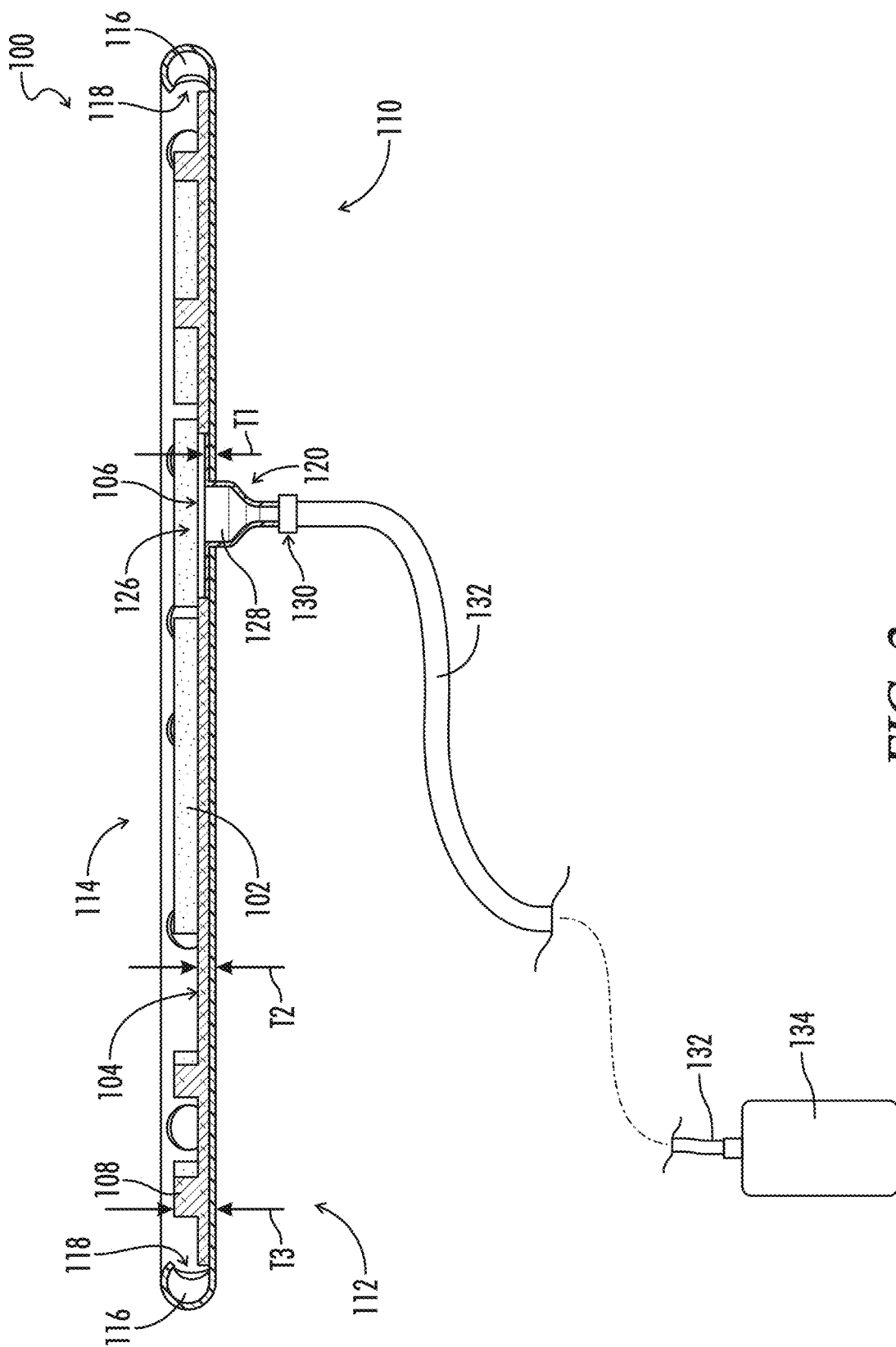
FIG. 2 is a cross-sectional side elevation view of the incontinence aid of FIG. 1.
Figure 3:
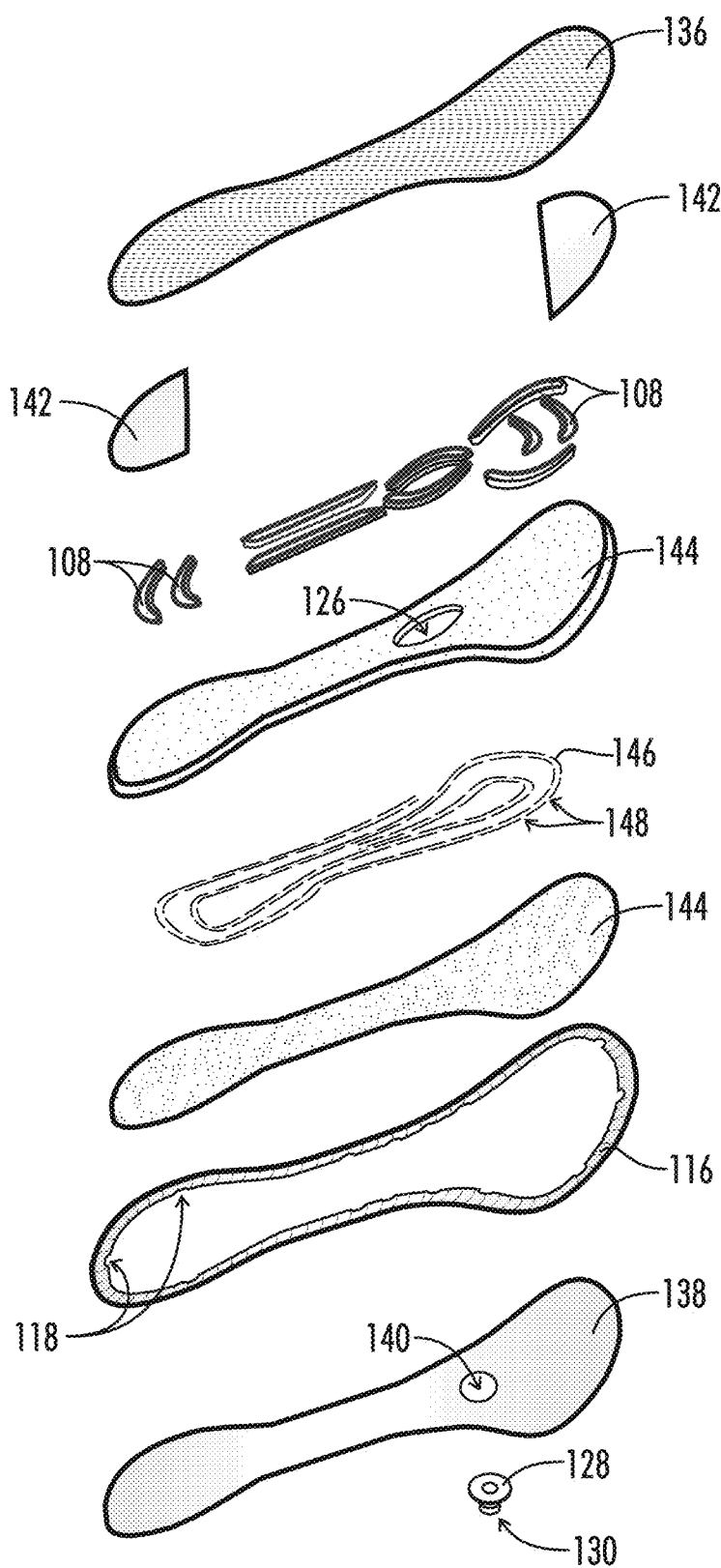
FIG. 3 is an exploded perspective view of the incontinence aid of FIG. 1.

Referring to FIG. 1, an embodiment of an incontinence aid 100 is shown. The incontinence aid 100 may be shaped and sized to fit a female. In some embodiments, the incontinence aid 100 may be shaped and sized to fit an adult woman. The incontinence aid 100 may be made of one or more sheet layers as shown in FIG. 3 and discussed in more detail below. In some embodiments, at least some of the layers may be absorbent. The incontinence aid 100 may be made of any appropriate material including cotton for washable embodiments, paper for disposable embodiments, or any other suitable materials. The incontinence aid 100 as shown in FIGS. 1-3 may be placed on an undergarment of a user. In particular, the incontinence aid 100 may include adhesive on the undergarment facing side of the incontinence aid or the incontinence aid may include one or more wings for taping the incontinence aid to the undergarment. The incontinence aid 100 may be of any appropriate grade for a desired absorbency including light, medium, or heavy absorbency, for instance. The incontinence aid 100 may be used as an undergarment liner, a pad, or even as a component permanently affixed to an incontinence undergarment.

The incontinence aid 100 may include a pad body 102. The pad body 102 may be made of any appropriate materials and may include a liquid receiving area 104.

The liquid receiving area 104 may include a liquid collection reservoir 106 defined in the pad body 102. In many embodiments, the liquid collection reservoir 106 may be formed by compressing the pad body 102 during manufacture. Of course, the liquid collection reservoir 106 may be formed by simply having a thinner portion of the pad body 102 or by the addition or removal of materials of the pad body. As shown in FIG. 1, some embodiments may include a liquid collection reservoir 106 of an approximately oval shape. All other shapes are also contemplated herein, however. As shown in FIG. 2, the liquid collection reservoir 106 may include a first thickness T1 of the pad body 102. Other portions of the pad body 102 may include a second thickness T2 that is greater than the first thickness T1. The liquid collection reservoir 106 may be the thinnest portion of the liquid receiving area 104 of the pad body 102.

The pad body 102 may further include at least one ridge 108. The one or more ridges 108 may be sized, shaped, and positioned such that they may aid in directing liquid to the liquid collection reservoir 106. For instance, the ridges 108 may include curved ridges for containing primary liquid flows that may otherwise splash or extend in an undesired direction, and the ridges may also include straight ridges for directing secondary liquid flows toward the liquid collection reservoir 106. In some embodiments, the ridges 108 may provide adequate spacing between the user's body and the liquid receiving area 104 to allow the liquid to move more freely toward the liquid collection reservoir 106. The at least one ridge 108 may include a third thickness T3 of the pad body 102. This third thickness T3 may be greater than the first thickness T1 and the second thickness T2.

In some embodiments, the pad body 102 may further include a front portion 110. The front portion 110 may be considered the portion of the pad body 102 that is placed adjacent the front side of a user. The front portion 110 may include a front portion width W1 defined as the maximum width of the front portion. The pad body 102 may also include a back portion 112. The back portion 112 may be considered the portion of the pad body 102 that is placed adjacent the back side of the user. The back portion 112 may be opposite the front portion 110. The back portion 112 may further include a back portion width W2 defined as the maximum width of the back portion. In many embodiments, the front portion width W1 may be greater than the back portion width W2. A possible benefit of such a configuration may be that the front portion 110 may be wider to accommodate more liquid through absorption due to the increased relative area compared to the back portion 112 because the liquid may tend to more likely engage the front portion than the back portion. The pad body 102 may further include a middle portion 114 disposed between the front portion 110 and the back portion 112. The middle portion 114 may include a middle portion width W3 defined as the minimum width of the middle portion. In many embodiments, the middle portion width W3 may be less than the front portion width W1 and the back portion width W2. In many embodiments, the pad body 102 may include a generally hourglass shape.

The incontinence aid 100 may further include a liquid passage 116 connected to the pad body 102. The liquid passage 116 may form a boundary about a majority of the liquid receiving area 104 in some embodiments. In other embodiments, the liquid passage 116 may form a boundary about the entire liquid receiving area 104. In many embodiments, the liquid passage 116 may include at least one lateral opening 118 defined in the lateral passage wall. The at least one lateral opening 118 may generally face the liquid receiving area 104. The lateral opening 118 may be any appropriate opening including, but not limited to, a cut or molded hole, a series of pores, a mesh section, a section of liquid permeable material, and the like. The liquid passage 116 may also include a water-resistant material or a waterproof material in some embodiments. In such embodiments, any liquid present in the liquid receiving area 104 may freely enter the liquid passage 116 via the at least one lateral opening 118. The liquid in the liquid passage 116 may be at least partially contained in the liquid passage alone, or it may be at least partially transferred along the liquid passage to another portion of the pad body 102 such as the liquid collection reservoir 106. This configuration may be useful for a user when she sits down, for instance. Sitting on all or a portion of the incontinence aid 100 may cause the liquid to be expressed from absorbent portions of the pad body 102 or may cause the liquid to otherwise move. The liquid may enter the liquid passage 116 instead of escaping from the incontinence aid 100 entirely when the user sits down. This rerouting of liquid may provide more complete containment of the liquid and thus may provide a more reliable incontinence aid 100.

As shown particularly in FIGS. 2 and 3, the incontinence aid 100 may further include a drain 120. The drain 120 may be connected to the pad body 102. This connection may be made in any appropriate manner, and the drain 120 may be of any appropriate construction. In some embodiments, the drain 120 may include a cut or molded hole, a series of pores, a mesh section, a section of liquid permeable material, and the like. The drain 120 may be configured to receive liquid from at least one of the liquid receiving area 104 and the liquid passage 116. In some embodiments, the drain 120 may be connected to the liquid receiving area 104 of the pad body 102. In at least one embodiment, the drain 120 may be connected to the pad body 102 at the liquid collection reservoir 106. In such embodiments, the ridges 108 and the liquid passage 116 may both help direct the liquid to the liquid collection reservoir 106. The drain 120 may then be configured to receive the liquid from the liquid collection reservoir 106 so the liquid may then be carried away from the pad body 102. The drain 120 may include a hole 126 defined in at least one layer of the pad body 102. The drain 120 may further include a funnel 128 to direct the liquid flow. Additionally or alternatively, the drain 120 may include a tubing connector end 130 to connect the drain to appropriate tubing 132. In some embodiments, the tubing connector end 130 may be similar or identical to a typical catheter tubing connector that are typically used to connect catheter tubing to a catheter. The tubing 132 may also, in some embodiments, be similar or identical to typical catheter tubing. One or more tubing clamps (not shown) may be disposed on the tubing 132 to close off the tubing as desired by the user. The incontinence aid 100 may also include at least one liquid retention vessel 134. The liquid retention vessel 134 may be located relatively remote from the pad body 102 while still being in fluid communication with the drain 120. In at least one embodiment, the tubing connector end 130 of the drain 120 may be connected to the liquid retention vessel 134, which may also include its own tubing connector, with the tubing 132. A non-limiting example of an appropriate liquid retention vessel 134 may be any known urinary leg bag, any known large capacity container that is typically placed next to the user while the user sleeps, and the like.

As mentioned briefly above, the incontinence aid 100 may include several layers as shown in FIG. 3. The incontinence aid 100 may include a skin engagement layer 136, for instance. The skin engagement layer 136 may be permeable to fluid such that fluid does not remain on or within the skin engagement layer. In some embodiments, the skin engagement layer 136 may include a material that may prevent skin irritation for the user.

The incontinence aid 100 may further include a waterproof layer 138. The waterproof layer 138 may be the layer of the incontinence aid 100 farthest from the user when worn by the user. Other embodiments may simply include the waterproof layer 138 being opposite the skin engagement layer 136. Additional layers may be disposed on one or both sides of the waterproof layer 138. The waterproof layer 138 may, in some embodiments, serve to aid direction of liquid toward the funnel 128 of the drain 120. The waterproof layer 138 may further aid in preventing liquid from escaping from the incontinence aid 100. In embodiments including the drain 120, the waterproof layer 138 may include a hole 140 defined therein to allow liquid to enter the funnel 128 of the drain.

In many embodiments, the incontinence aid 100 may include waterproof endcap portions 142. The waterproof endcap portions 142 may be connected to the waterproof layer 138. In some embodiments, the waterproof endcap portions 142 may be connected along the outer perimeter to the waterproof layer 138 much like a front portion of a house slipper. Other layers may be disposed between the waterproof endcap portions 142 and the waterproof layer 138 where the waterproof endcap portions are not connected to the waterproof layer. The waterproof endcap portions 142 may be disposed under the skin engagement layer 136 in many embodiments. The function of the waterproof endcap portions 142 in some embodiments may be to prevent liquid contained within the pad body 102 from traveling toward a user or otherwise away from the pad body when the user sits or otherwise compresses a portion of the pad body.

One or more absorbent layers 144 may be disposed between the skin engagement layer 136 and the waterproof layer 138. The absorbent layers 144 may be configured to retain liquid in any appropriate manner.

In some embodiments of the incontinence aid 100, an internal liquid passage 146 may be disposed between the skin engagement layer 136 and the waterproof layer 138. In many embodiments, the internal liquid passage 146 may be disposed between absorbent layers 144. The internal liquid passage 146 may be similar in construction to the liquid passage 116 discussed above. In some embodiments, the internal liquid passage 146 may be smaller in diameter than the liquid passage 116 discussed above. The internal liquid passage 146 may further include lateral openings 148 defined internal liquid passage wall. The internal liquid passage 146 may receive liquid from any portion of the pad body 102 where liquid may pool or be expressed. The internal liquid passage 146 may aid the transfer of the liquid to other portions of the pad body 102 to more effectively contain the liquid when compared to prior art incontinence aids. In some embodiments, the hole 126 in the pad body 102, or in the absorbent layer 144, may allow liquid disposed in the liquid collection reservoir 106 to more readily enter the internal liquid passage 146. In many embodiments, the internal liquid passage 146 may be exposed in the area of the liquid collection reservoir 106, such that the internal liquid passage is part of the liquid collection reservoir.

Figure 4:
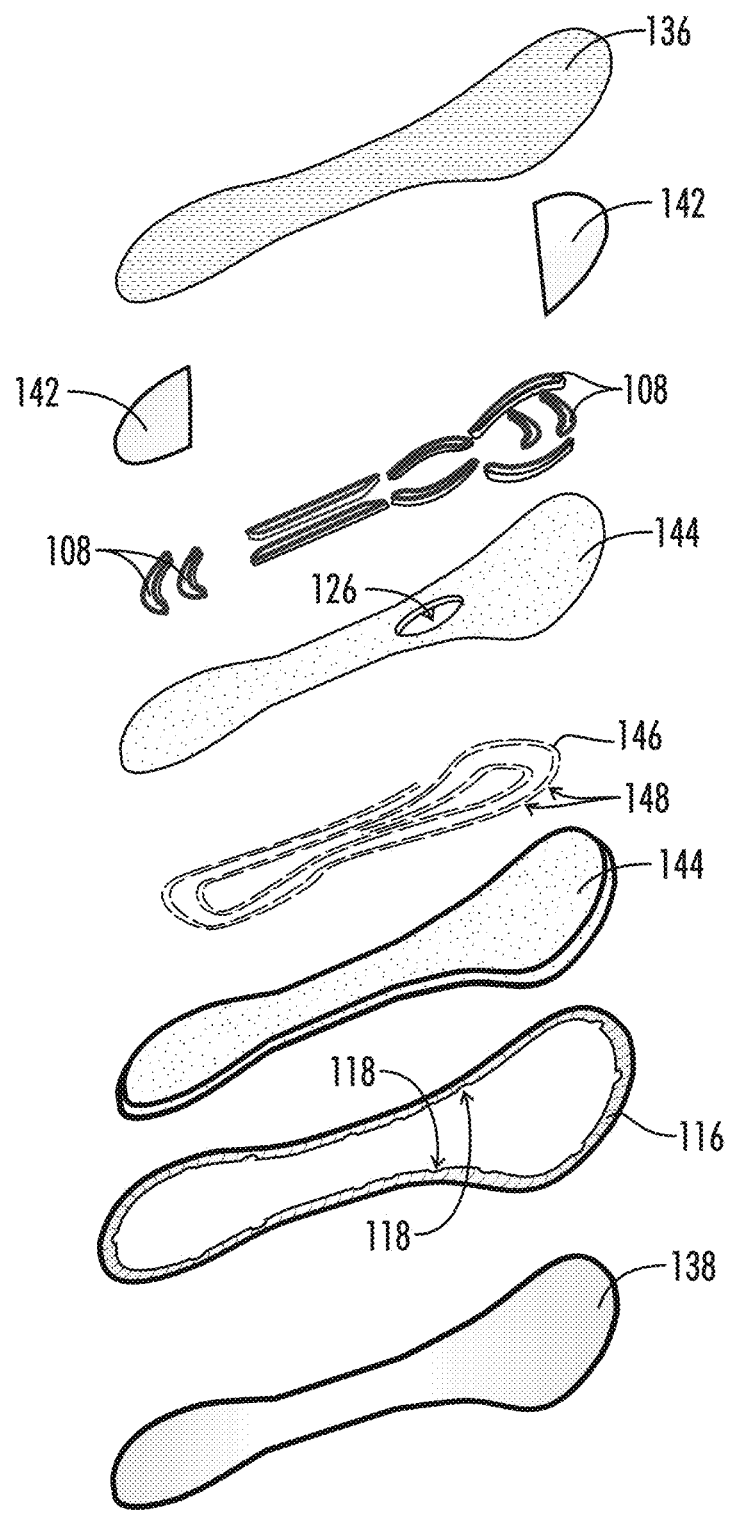
FIG. 4 is an exploded perspective view of another embodiment of an incontinence aid.

Of course, the incontinence aid 100 may not necessarily include a drain 120. In such embodiments, as shown in FIG. 4, the hole 126 defined in the pad body 102 may only direct liquid to the internal liquid passage 146 for redistribution. Also, the absorbent layers 144 may be arranged the same or differently from the embodiment shown in FIG. 3. The absorbent layers 144 may include layers of differing, similar, or identical thicknesses. The absorbent layers 144 may also be of the same, similar, or different materials.

Figure 5:
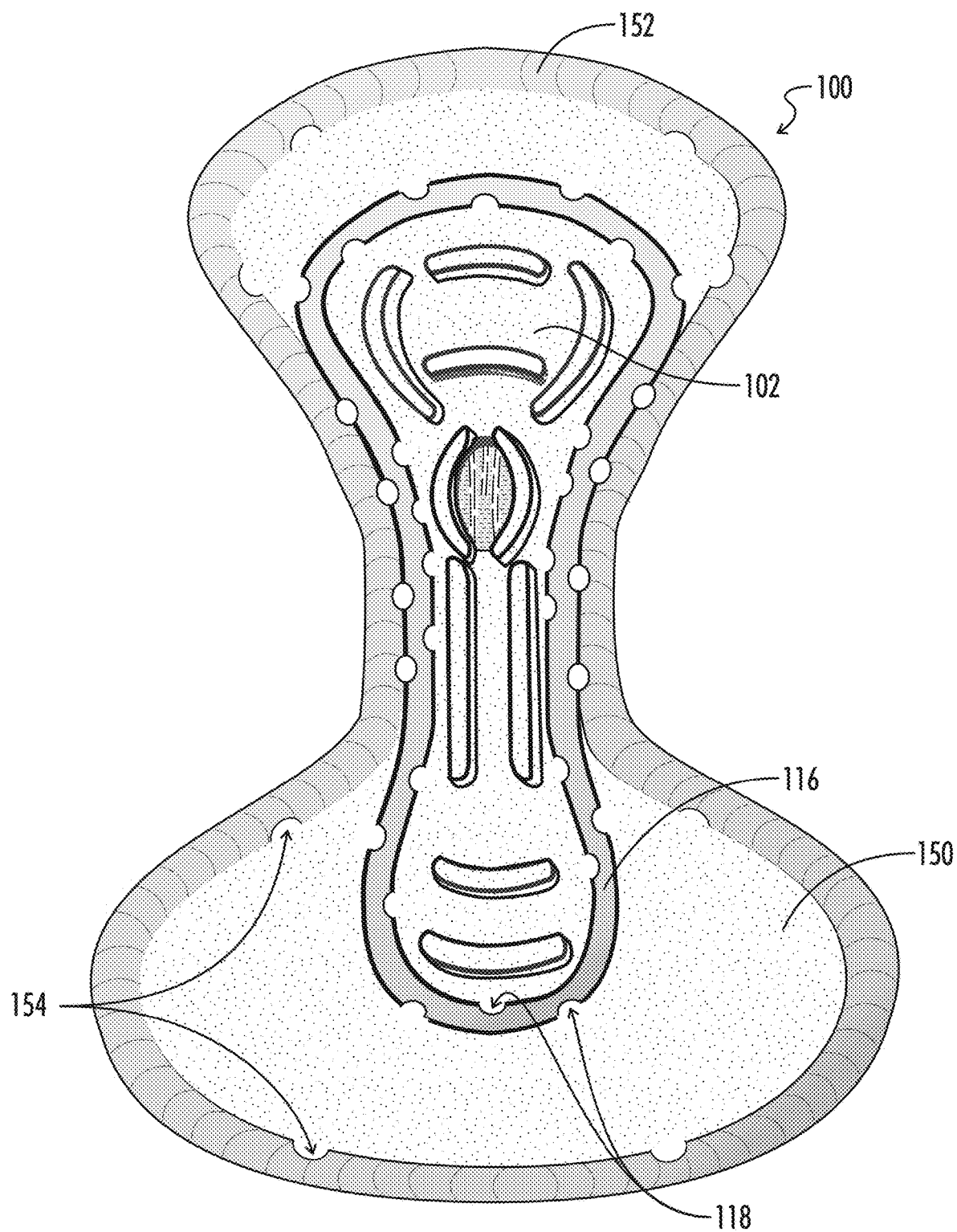
FIG. 5 is a front elevation view of an interior side of another embodiment of an incontinence aid.
Figure 6:
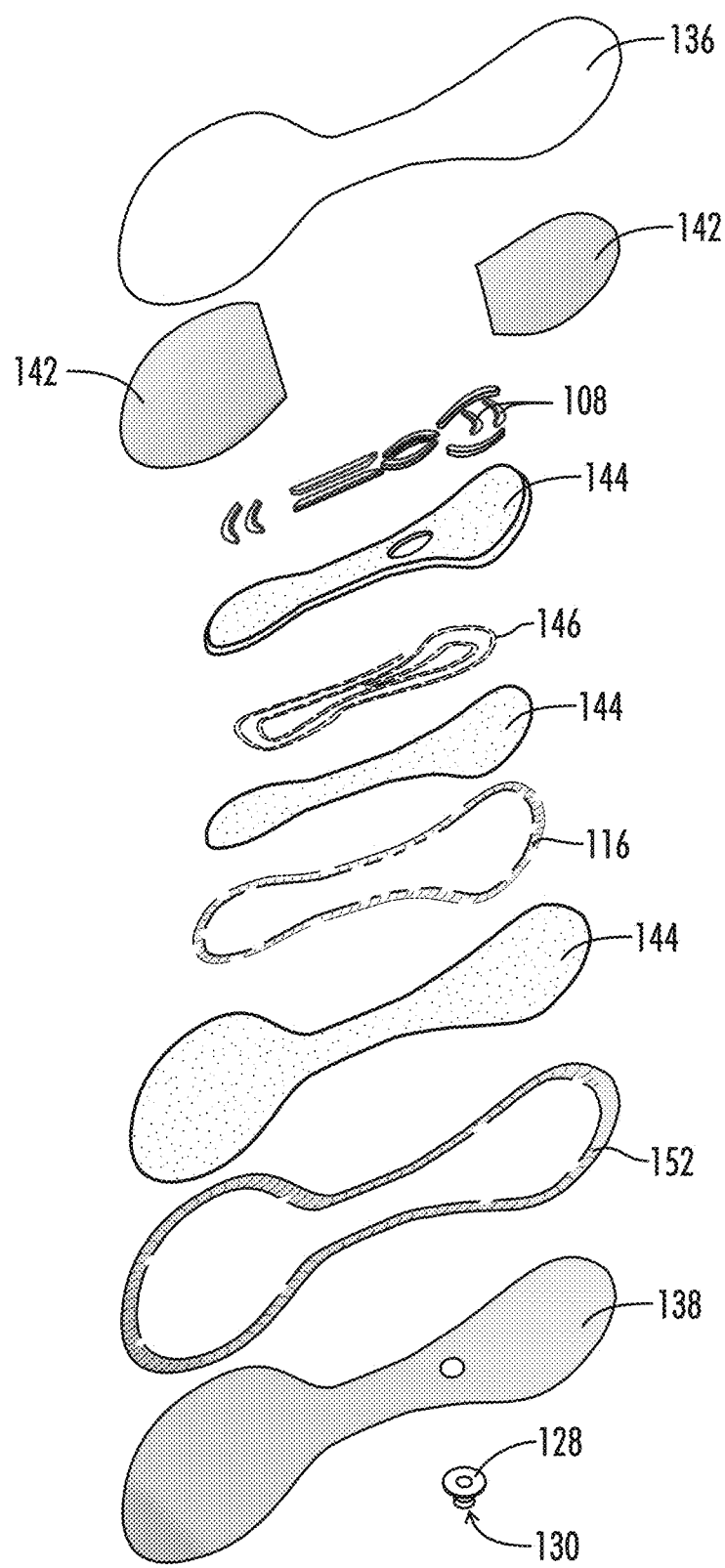
FIG. 6 is an exploded perspective view of the incontinence aid of FIG. 5.

Turning now to FIGS. 5 and 6, the incontinence aid 100 may further include a second pad body 150. The second pad body 150 may receive the pad body 102 discussed above thereon. The second pad body 150 may be larger in at least some areas than the pad body 102 discussed above. In the embodiment shown in FIGS. 5 and 6, the liquid passage 116 may include lateral openings 118 on both sides of the liquid passage instead of only on the inside. This modification may allow liquid received on the second pad body 150 to enter the pad body 102 discussed above and vice versa. The second pad body 150 may further include a second liquid passage 152 connected to the second pad body. The second liquid passage 152 may border all, or at least a majority, of the second pad body 150. The second liquid passage 152 may be similar in construction to the liquid passage 116 described above. In some embodiments, the second liquid passage 152 may include a greater diameter than the liquid passage 116 described above. The second liquid passage 152 may also include one or more lateral openings 154 as discussed above. In some embodiments, some of the lateral openings 154 of the second liquid passage 152 may face, or may be at least partially aligned with, the outward facing lateral openings 118 of the liquid passage 116. The addition of the second pad body 150 may be beneficial for a user who wishes to sleep while wearing the incontinence aid 100. The additional surface area and additional absorbent material may allow for a greater amount of liquid to be appropriately contained than other embodiments discussed above. In some of the embodiments of the incontinence aid 100 including the second pad body 150, the skin engagement layer 136, the waterproof layer 138, and the waterproof endcap portions 142 may be sized and positioned to surround both the smaller pad body 102 and the second pad body as shown in FIG. 6.

Turning now to FIGS. 7-13, the present disclosure also relates to an incontinence aid 200. The incontinence aid 200 may be shaped and sized to fit a male. In some embodiments, the incontinence aid 200 may be shaped and sized to fit an adult man. Many of the components and materials of the incontinence aid 200 may be similar to or the same as the components and materials of the incontinence aid 100 discussed above. In order to avoid redundancy, same or similar components of the incontinence aid 200 may be numbered a value of one hundred higher than the corresponding respective components of the incontinence aid 100, and these higher numbered components may not be discussed explicitly herein.

Figure 7:
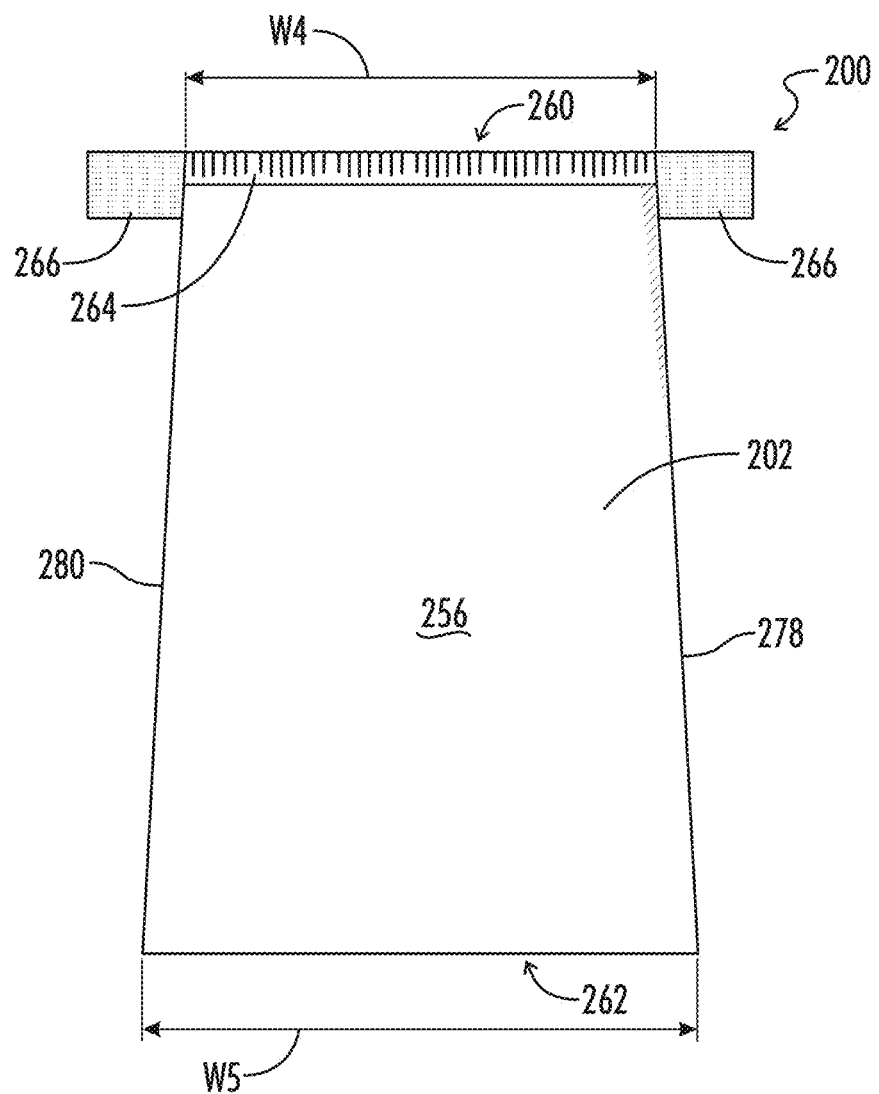
FIG. 7 is a front elevation view of another embodiment of an incontinence aid.
Figure 8:
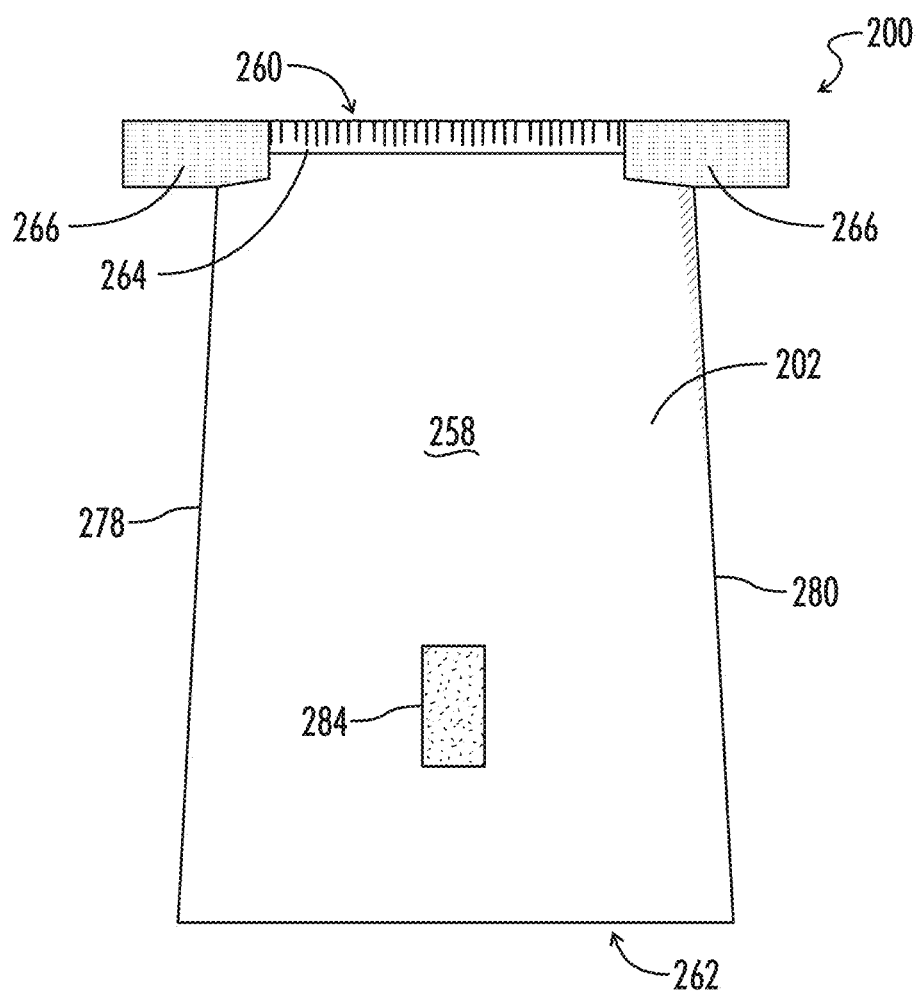
FIG. 8 is a rear elevation view of an exterior side of the incontinence aid of FIG. 7.
Figure 9:
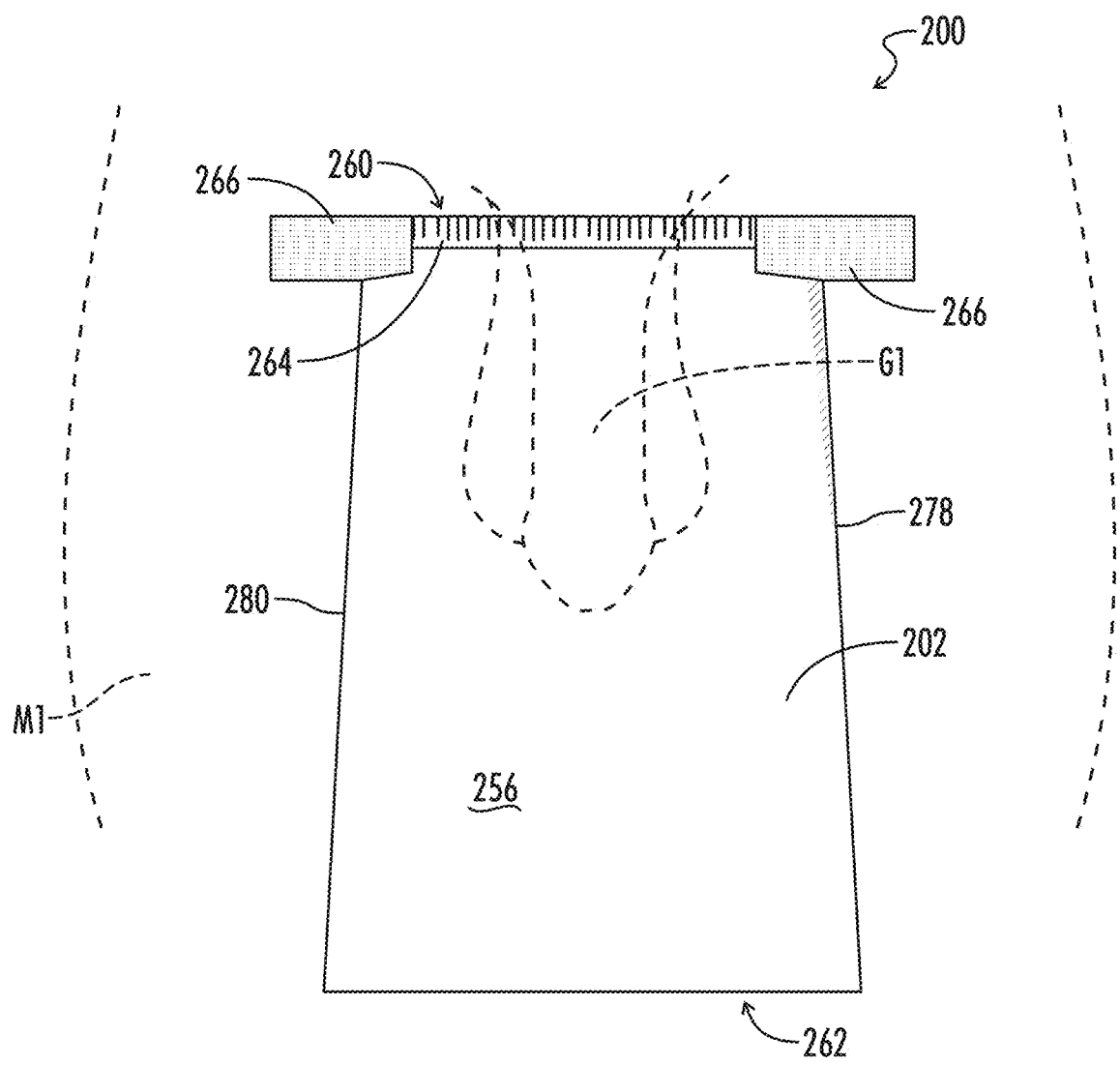
FIG. 9 is a front elevation view of the incontinence aid of FIG. 7 in position to be attached to the user.

The incontinence aid 200 may include a pad body 202. In some embodiments, the pad body 202 may generally resemble a sheet when in the unfolded position as shown in FIG. 7. The pad body 202 may include an interior side 256 and an exterior side 258 opposite the interior side. These names for the sides 256, 258 are for clarity purposes and do not reflect a particular configuration requirement in all embodiments of the incontinence aid 200. In some embodiments, however, at least a portion of the interior side 256 of the pad body 202 may be configured to face or make contact with the user's genitals G1 as shown in FIGS. 7-13. In such embodiments, at least a portion of the exterior side 258 of the pad body 202 may be configured to face away from the user's genitals G1 as shown in FIGS. 10-13. The pad body 202 may further include a proximal end 260 and a distal end 262 opposite the proximal end. These names for the ends 260, 262 are for clarity purposes and do not reflect a particular configuration requirement in all embodiments of the incontinence aid 200. In some embodiments, however, the proximal end 260 of the pad body 202 may be configured to be placed nearer the user than the distal end 262 of the pad body when positioned as shown in FIG. 9. The proximal end 260 of the pad body 202 may include a proximal end width W4, and the distal end 262 of the pad body may include a distal end width W5. In some embodiments, the distal end width W5 may be greater than the proximal end width W4. This width difference may allow the incontinence aid 200 to be more easily fitted on or about the user's genitals G1.

Many embodiments may include at least a portion of the proximal end 260 of the pad body 202 being at least somewhat elastic relative to the rest of the pad body. This elasticity may allow for more of a fitting tolerance to provide a better and/or more secure fit of the incontinence aid 200 about the user's genitals G1. In some embodiments, an elastic band 264 may be connected to the pad body 202 nearer the proximal end 260 of the pad body than the distal end 262 of the pad body. In further embodiments, the elastic band 264 may be connected to the pad body 202 adjacent the proximal end 260 of the pad body.

Figure 11:
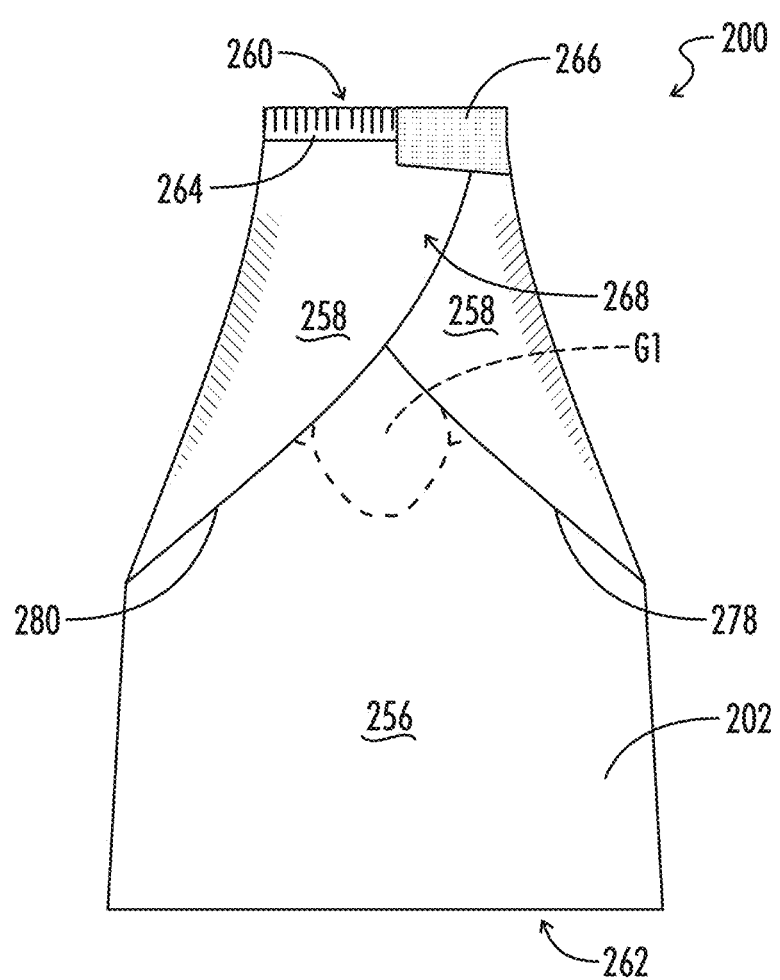
FIG. 11 is a front elevation view of the incontinence aid of FIG. 7 in a further subsequent step of attachment to the user.

The incontinence aid 200 may further include a first fastener 266 permanently connected to the pad body 202 nearer the proximal end 260 of the pad body than the distal end 262 of the pad body. In many embodiments, the first fastener 266 may be permanently connected to the pad body 202 adjacent the proximal end 260 of the pad body. The first fastener 266 may be configured to removably attach a first overlapping portion 268 of the pad body 202 adjacent the proximal end 260 of the pad body to the exterior side 258 of the pad body adjacent the proximal end of the pad body. Stated another way, the pad body 202 may be folded over near the proximal end 260 of the pad body to form a first overlapping portion 268 of the pad body adjacent the proximal end of the pad body as shown in FIG. 11. This first overlapping portion 268 of the pad body 202 may be secured in place with the first fastener 266. The first fastener 266 may include any appropriate fastener as contemplated above.

Figure 12:
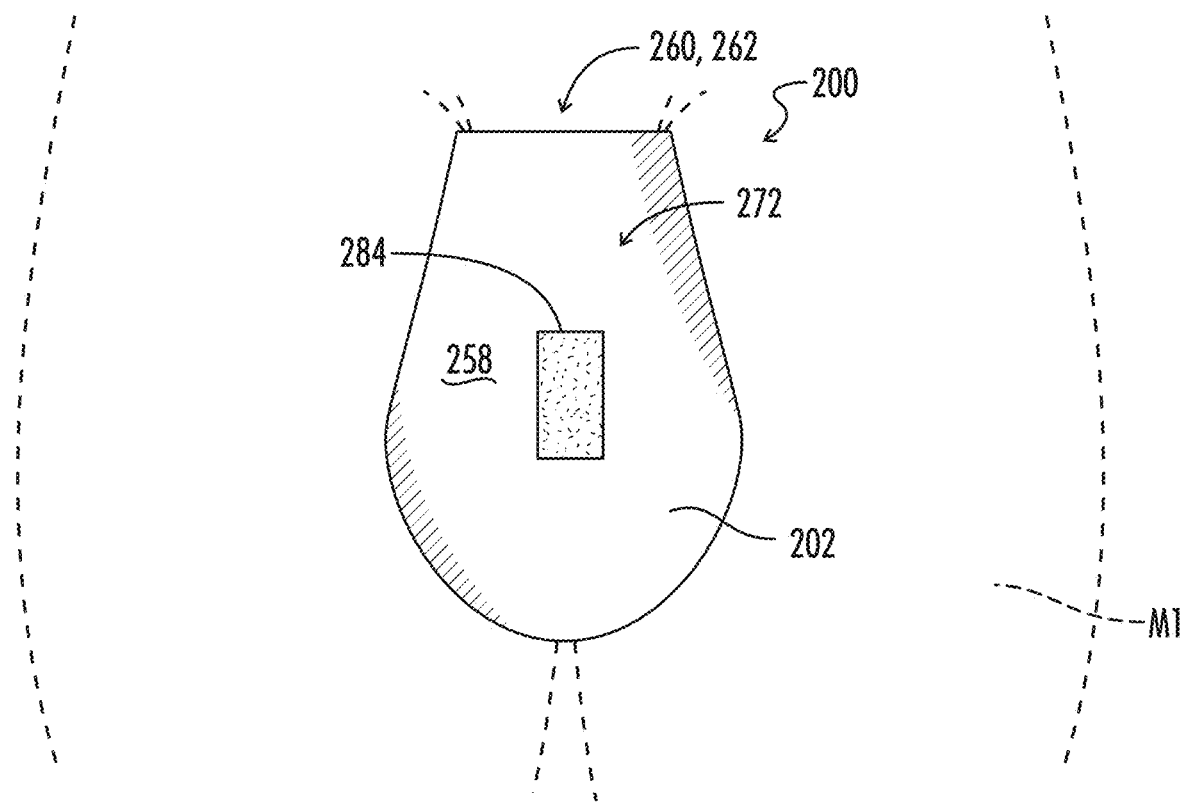
FIG. 12 is a front elevation view of the incontinence aid of FIG. 7 attached to the user.
Figure 13:
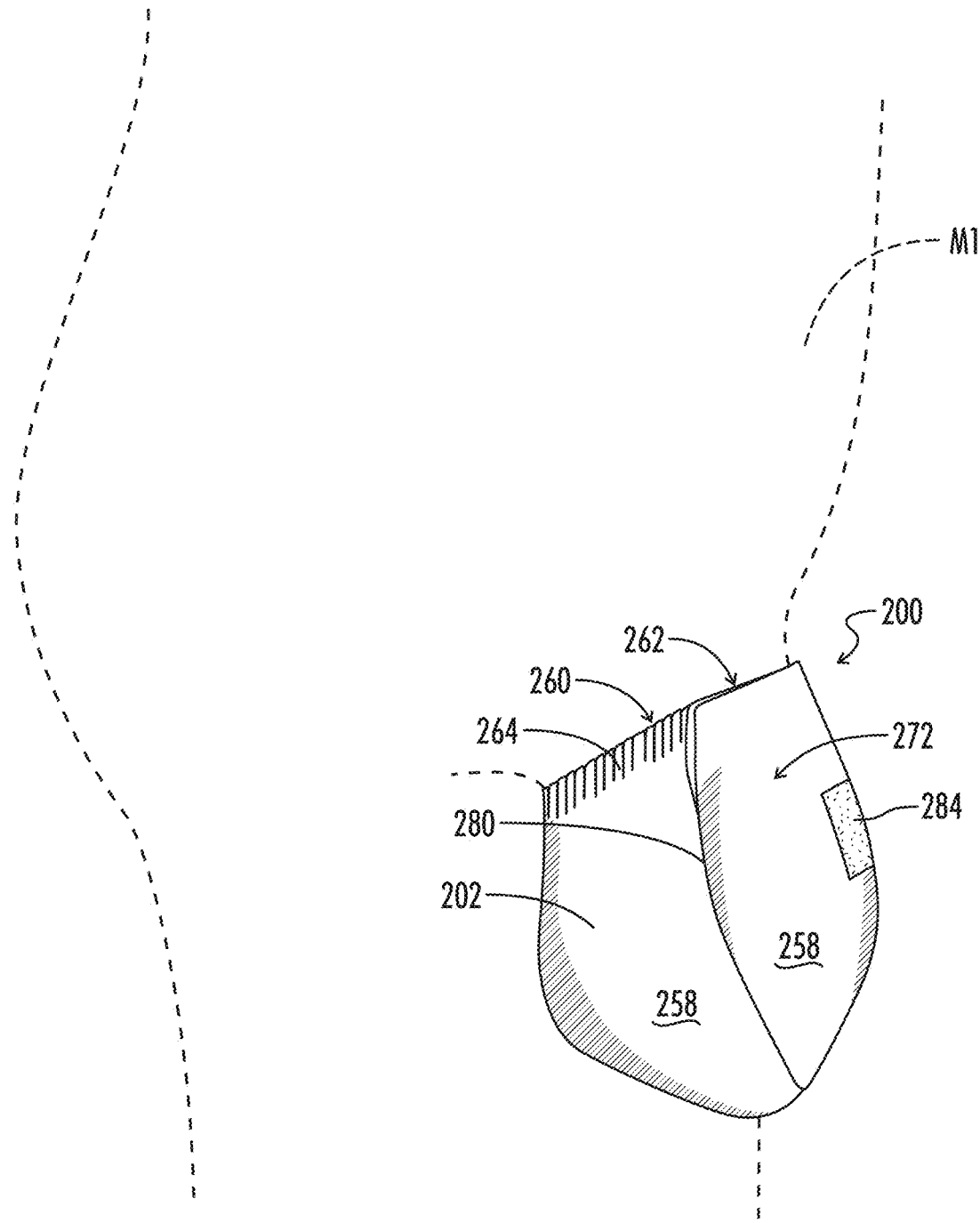
FIG. 13 is a side elevation view of the incontinence aid of FIG. 7 attached to the user.
Figure 14:
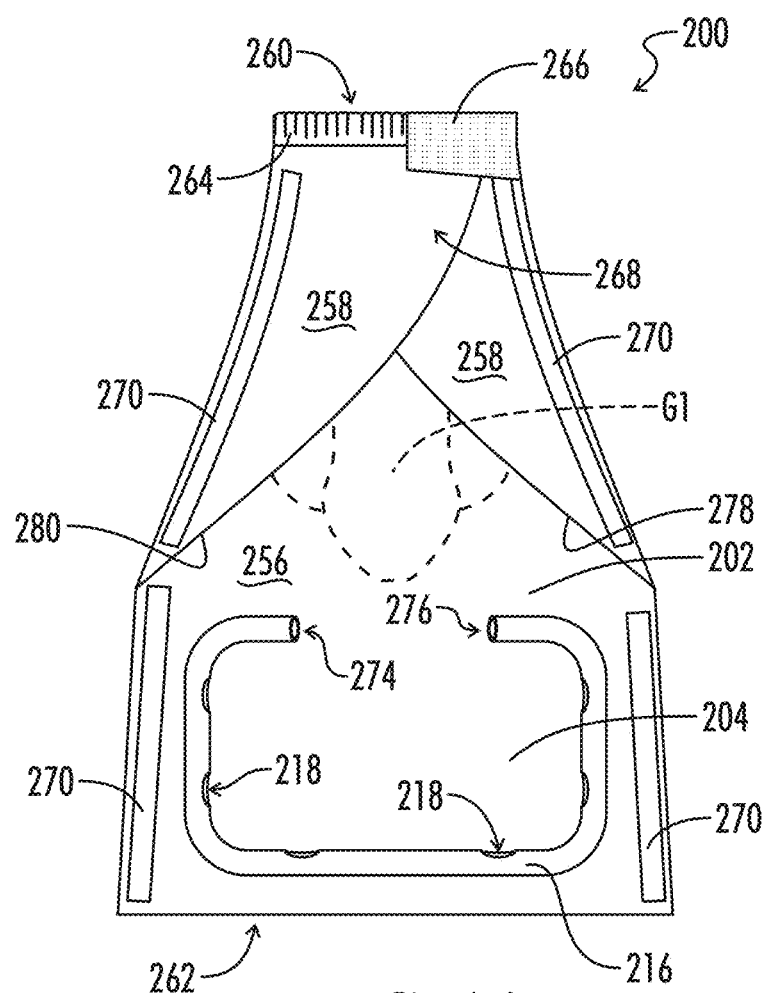
FIG. 14 is a front elevation view of another embodiment of an incontinence aid during attachment to a user.
Figure 15:
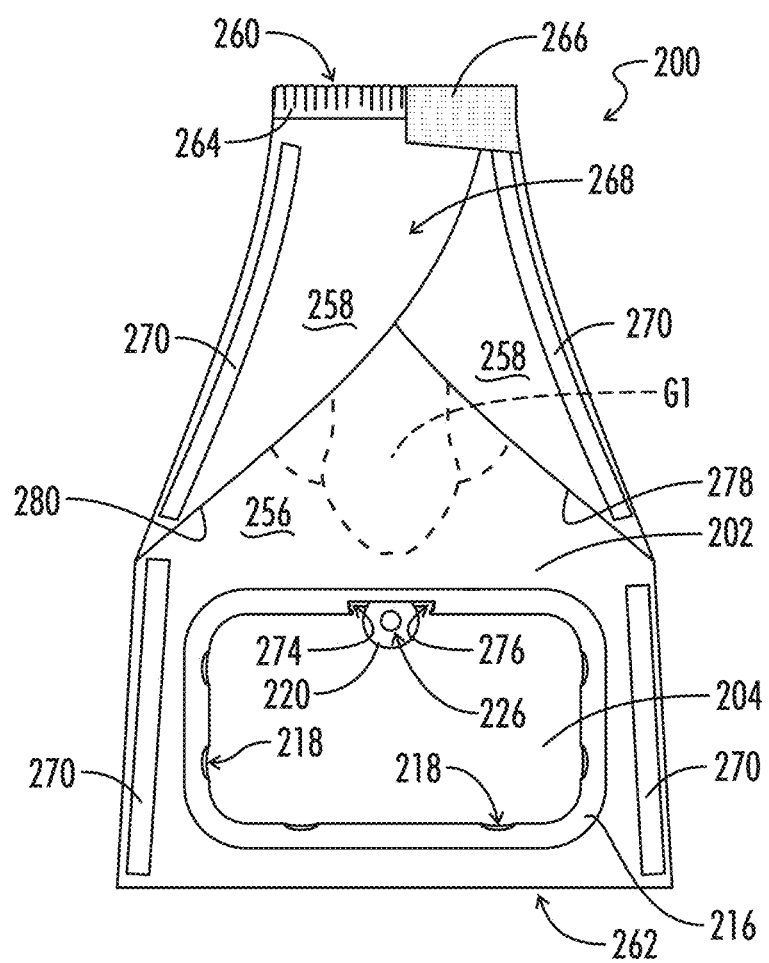
FIG. 15 is a front elevation view of yet another embodiment of an incontinence aid during attachment to a user.
Figure 16:
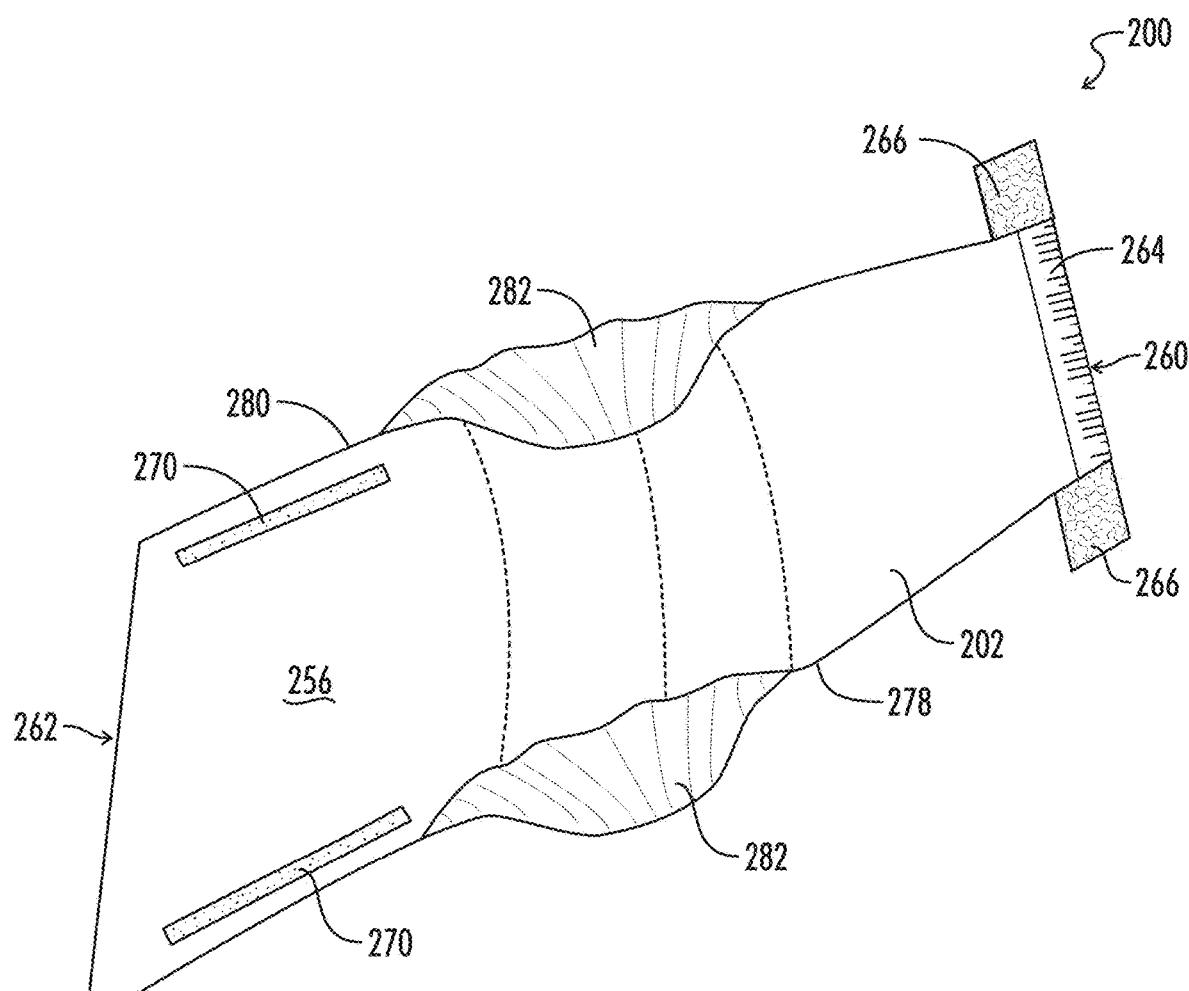
FIG. 16 is a perspective view of another embodiment of an incontinence aid.

As best shown in FIGS. 14 and 15, many embodiments of the incontinence aid 200 may also include a second fastener 270 permanently connected to the pad body 202 nearer the distal end 262 of the pad body than the first fastener 266. In some embodiments, the second fastener 270 may be permanently connected to the pad body 202 adjacent the distal end 262 of the pad body. As shown in FIGS. 12 and 13, the second fastener 270 may be configured to removably attach a second overlapping portion 272 of the pad body 202 adjacent the distal end 262 of the pad body to the exterior side 258 of the pad body. Stated another way, the pad body 202 may be folded over between the proximal end 260 of the pad body 202 and the distal end 262 of the pad body to form a second overlapping portion 272 of the pad body as shown in FIGS. 12 and 13. This second overlapping portion 272 of the pad body 202 may be secured in place with the second fastener 270. The second fastener 270 may include any appropriate fastener as contemplated above.

Some embodiments of the incontinence aid 200 may include the liquid passage 216 as shown in FIGS. 14 and 15. As shown in FIG. 14, the liquid passage 216 may include a section of the passage having no lateral openings 218.

In another embodiment shown in FIG. 15, the liquid passage 216 may include a first liquid passage open end 274 and a second liquid passage open end 276. In at least one of these embodiments, the drain 220 may be connected to the pad body 202 between the first liquid passage open end 274 and the second liquid passage open end 276. As such, at least some of the liquid may be carried to the drain 220 via the liquid passage 216. Of course, liquid may also reach the drain 220 directly from the liquid receiving area 204 in many embodiments.

Figure 10:
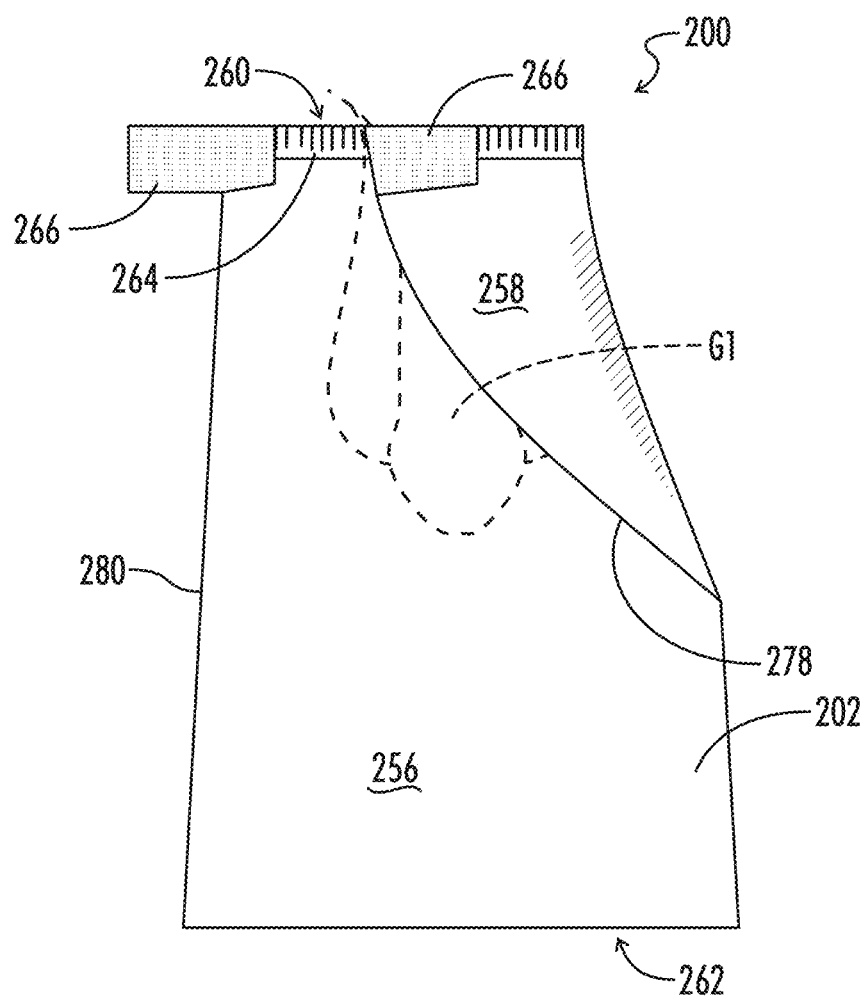
FIG. 10 is a front elevation view of the incontinence aid of FIG. 7 in a subsequent step of attachment to the user.

Illustrated particularly in FIGS. 9-12, the present disclosure further relates to a method of attaching an incontinence aid 200 to a man M1. The method may include positioning a pad body 202 of the incontinence aid 200 such that an interior side 256 of the pad body adjacent a proximal end 260 of the pad body is under the man's genitals G1 (as shown in FIG. 9). The method may further include folding a first side edge 278 of the pad body 202 over at least a portion of the man's genitals G1 such that the interior side 256 of the pad body adjacent the proximal end 260 of the pad body and adjacent the first side edge of the pad body faces at least a portion of the man's genitals (as shown in FIG. 10). The method may also include folding a second side edge 280 of the pad body 202 over the first side edge 278 of the pad body such that the interior side 256 of the pad body adjacent the proximal end 260 of the pad body and adjacent the second side edge of the pad body faces at least a portion of the exterior side 258 of the pad body adjacent the proximal end of the pad body and adjacent the first side edge of the pad body (as shown in FIG. 11). The method may further still include folding the pad body 202 such that the interior side 256 of the pad body adjacent a distal end 262 of the pad body faces at least a portion of the exterior side 258 of the pad body to cover the man's genitals G1 (as shown in FIGS. 12 and 13). The method may even further include securing the pad body 202 in a folded position (as shown in FIGS. 12 and 13) to retain the pad body on the man's genitals G1.

In some embodiments of the method described above, the method may further include fastening the interior side 256 of the pad body 202 adjacent the proximal end 260 of the pad body and adjacent the second side edge 280 of the pad body to the exterior side 258 of the pad body adjacent the proximal end of the pad body and adjacent the first side edge 278 of the pad body. This step may allow the incontinence aid 200 to be retained on the man's genitals G1 as shown in FIG. 11 without the man M1 or another user being forced to hold the incontinence aid in place prior to further securing the incontinence aid.

Further embodiments of the method may also include fastening the interior side 256 of the pad body 202 adjacent the distal end 262 of the pad body to the exterior side 258 of the pad body.

In even further embodiments, the interior side 256 of the pad body 202 adjacent the distal end 262 of the pad body may be fastened to the exterior side 258 of the pad body adjacent the proximal end 260 of the pad body.

As shown in FIGS. 16-22, the incontinence aid 200 may further include web sections 282 disposed on both side edges 278, 280 of the pad body 202. The web sections 282 may include a water-resistant or water-proof material in some embodiments. The web sections 282 may facilitate folding the incontinence aid 200 into the final position as shown in FIGS. 12 and 13. The web sections 282 may further prevent leakage of fluid contained by the incontinence aid 200 that may otherwise occur due to user movement or other disturbances to the incontinence aid.

Figure 17:
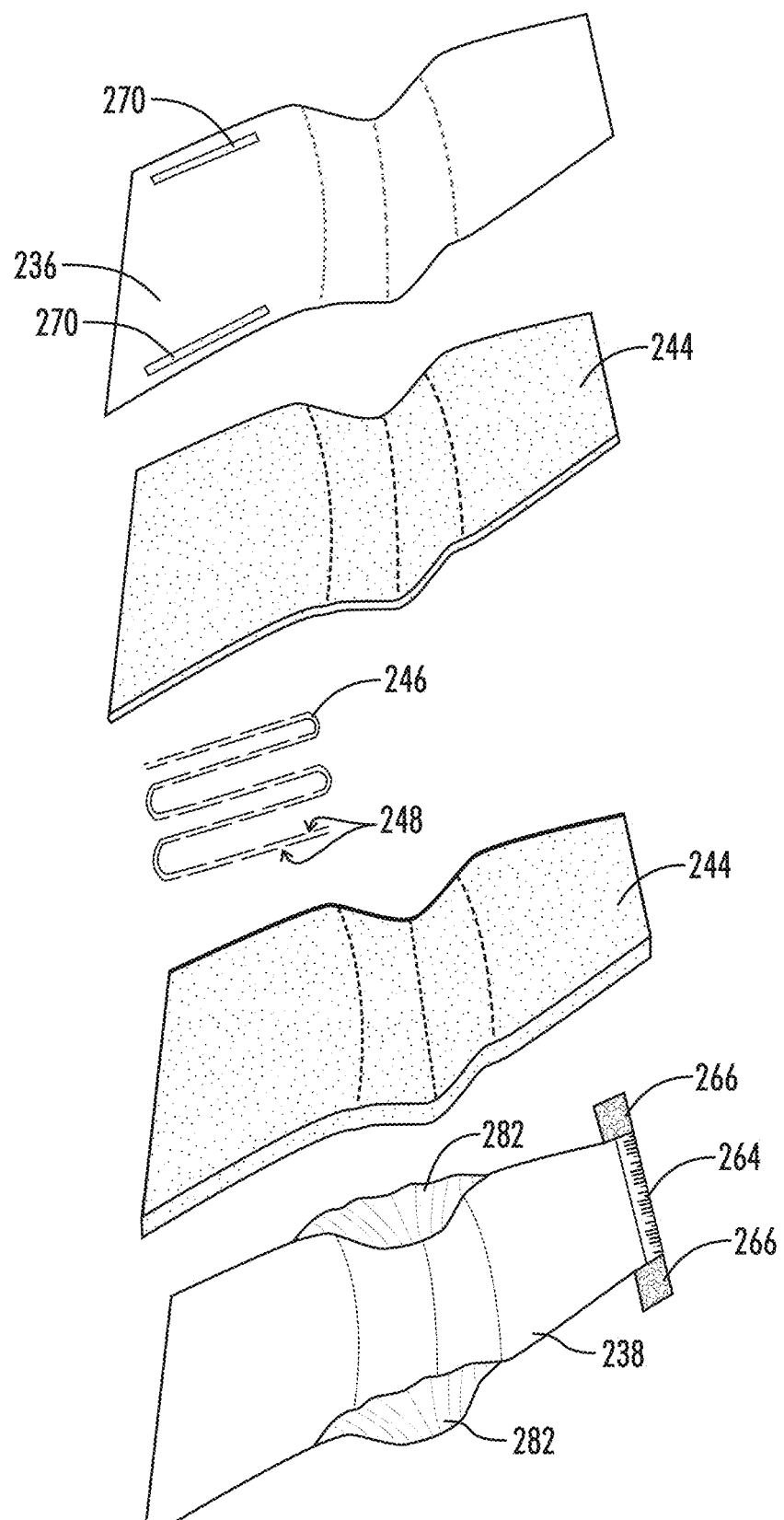
FIG. 17 is an exploded perspective view of the incontinence aid of FIG. 16.
Figure 18:
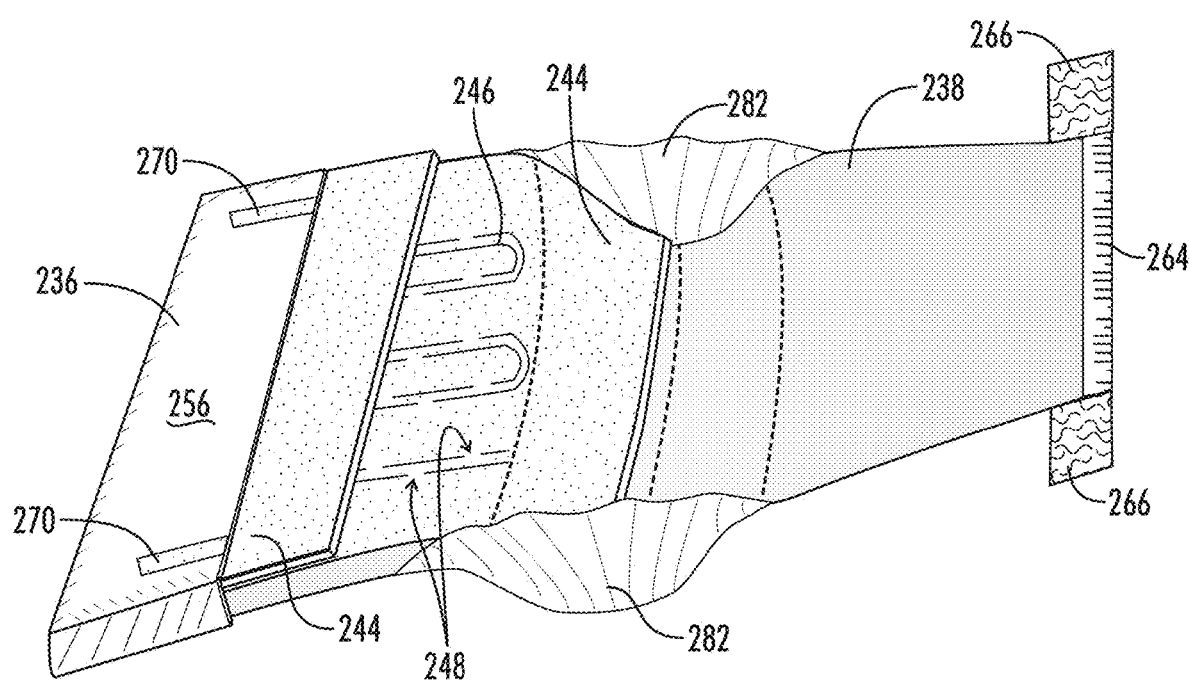
FIG. 18 is a perspective cutaway view of the incontinence aid of FIG. 16.
Figure 19:
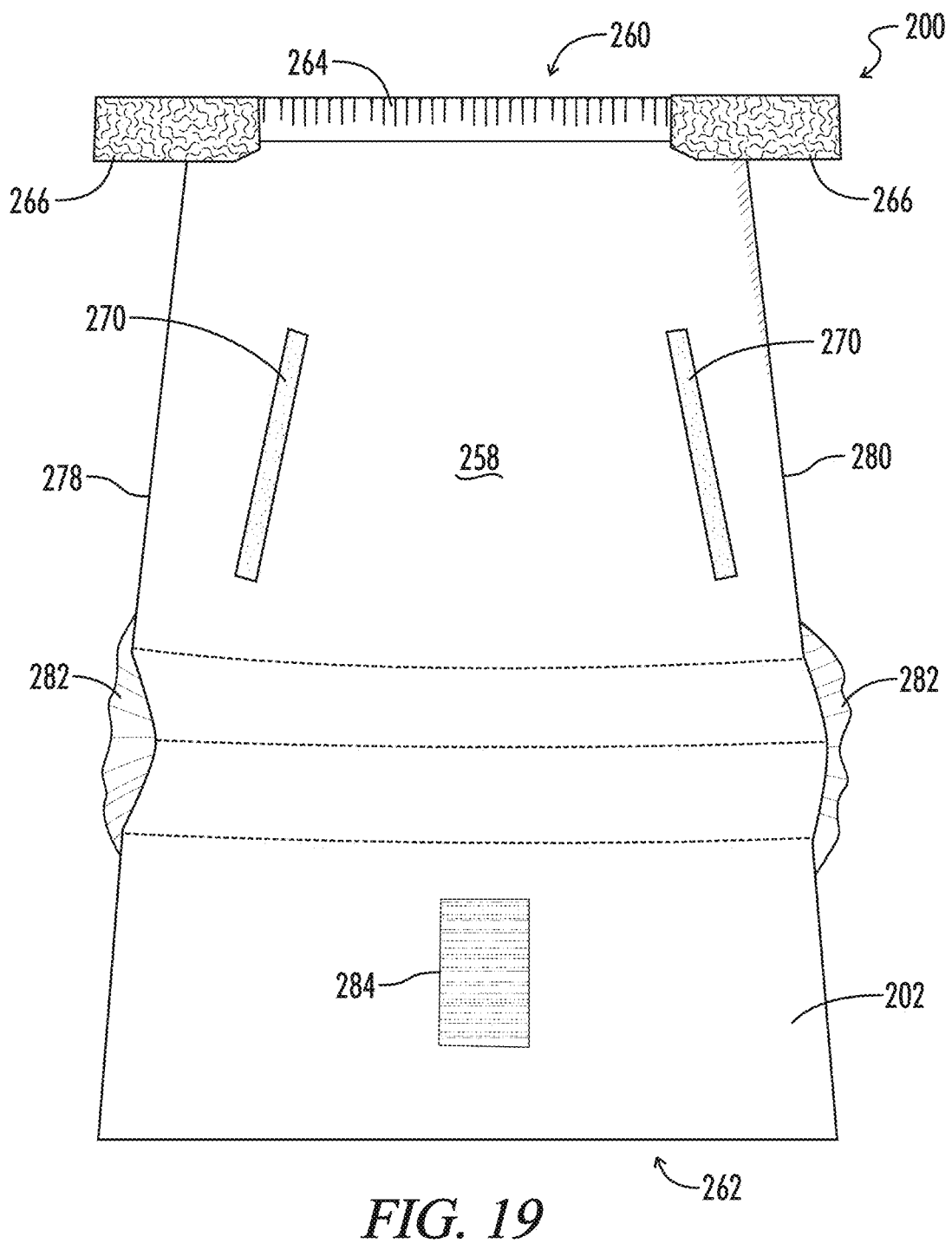
FIG. 19 is a rear elevation view of the incontinence aid of FIG. 16.
Figure 20:
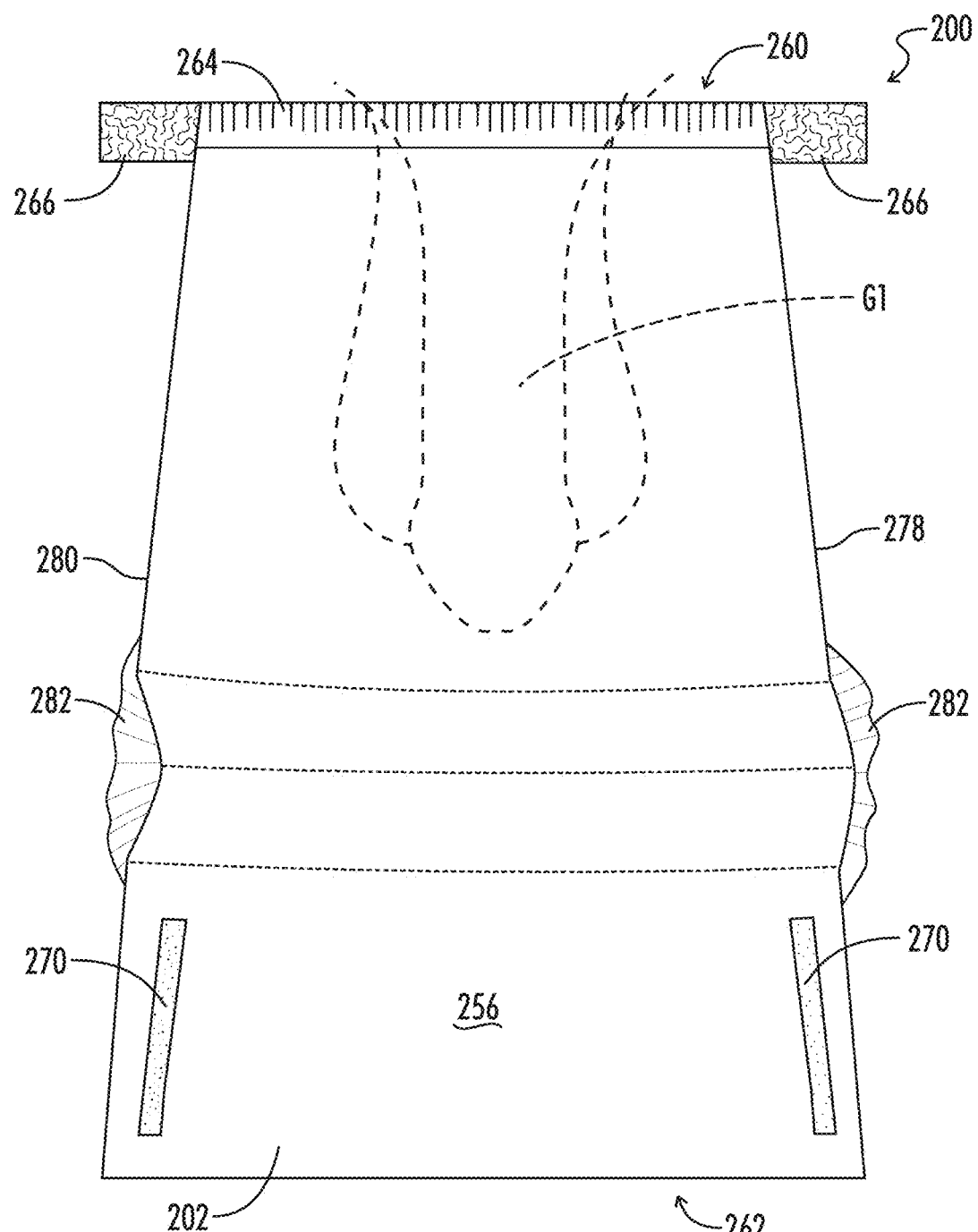
FIG. 20 is a front elevation view of the incontinence aid of FIG. 16 in position to be attached to the user.
Figure 21:
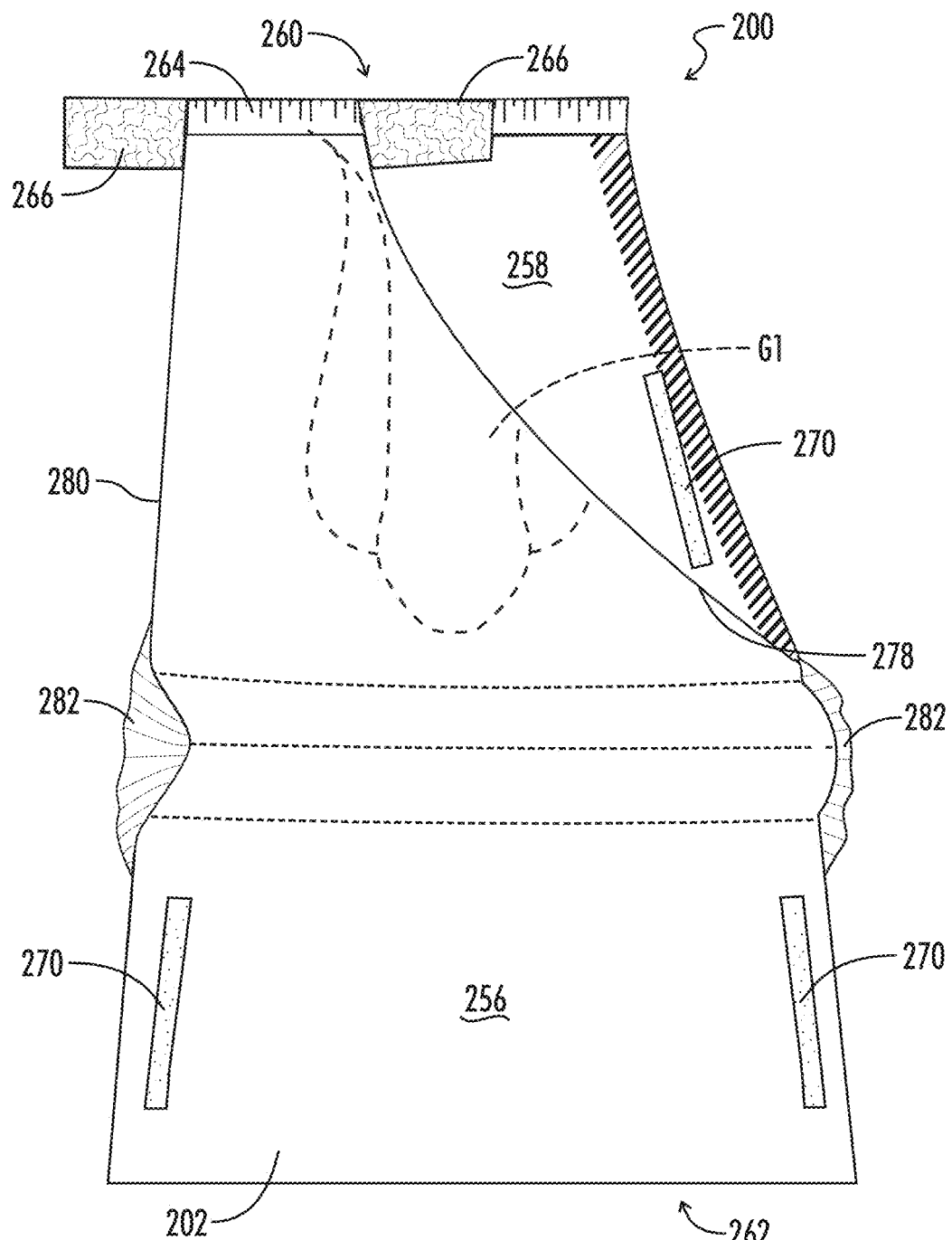
FIG. 21 is a front elevation view of the incontinence aid of FIG. 16 in a subsequent step of attachment to the user.
Figure 22:
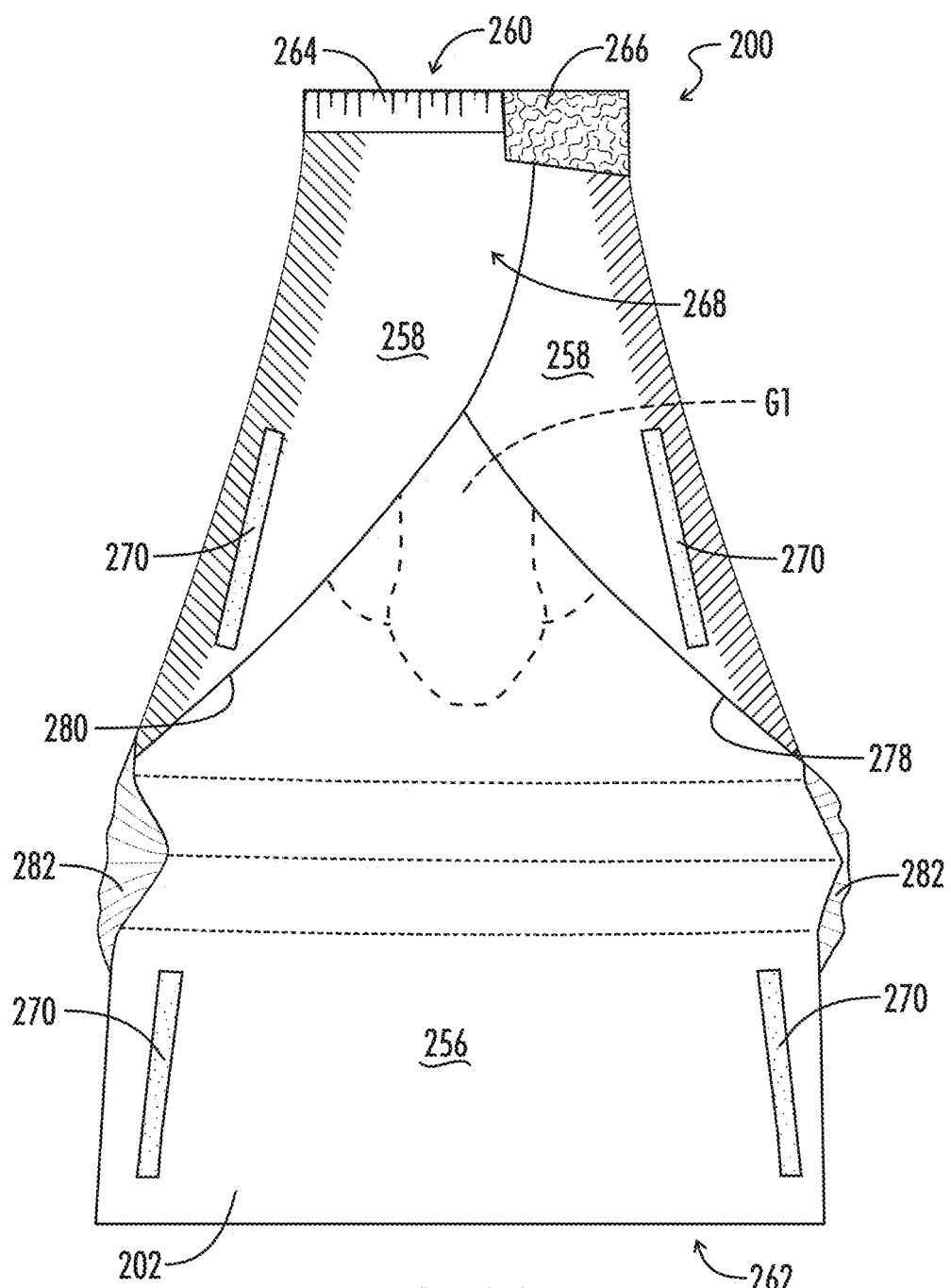
FIG. 22 is a front elevation view of the incontinence aid of FIG. 16 in a further subsequent step of attachment to the user.
Figure 23:
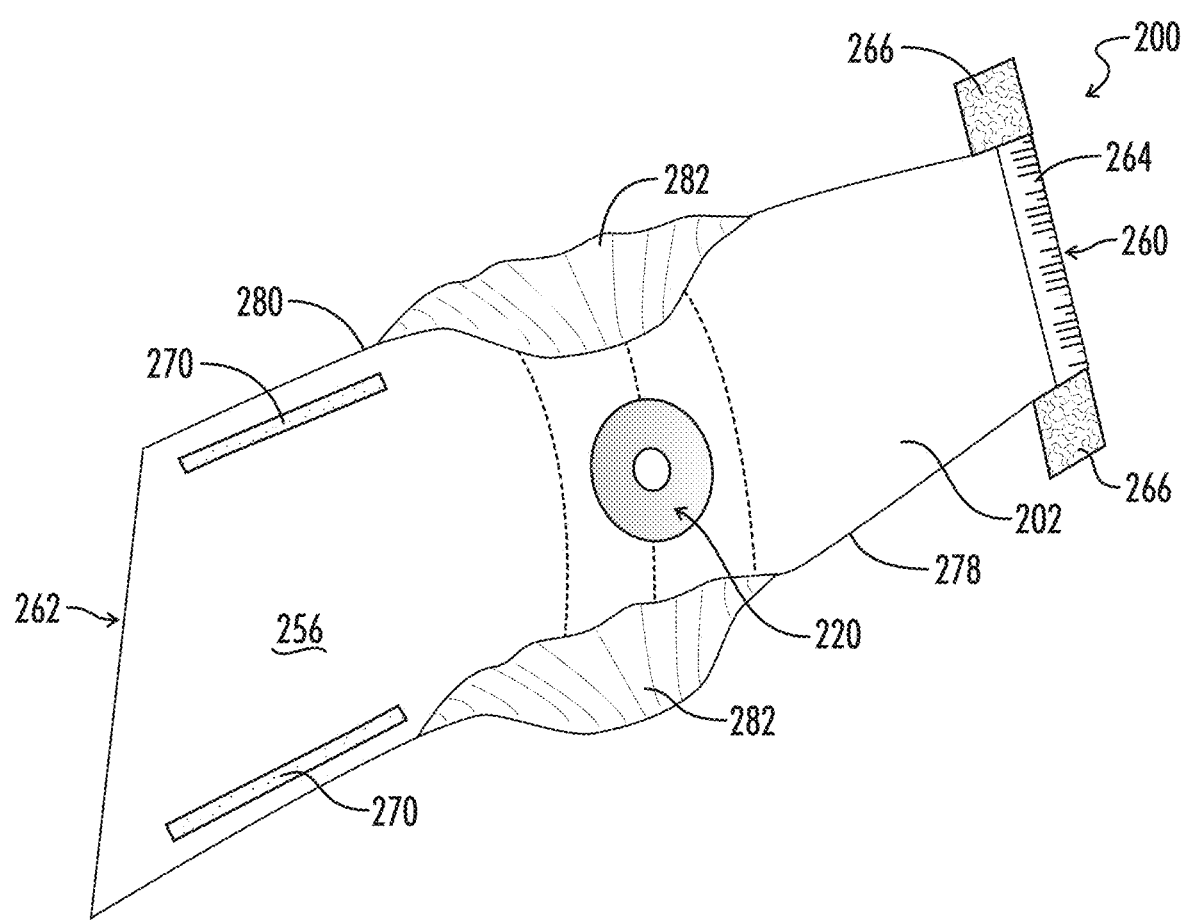
FIG. 23 is a perspective view of another embodiment of an incontinence aid.
Figure 24:
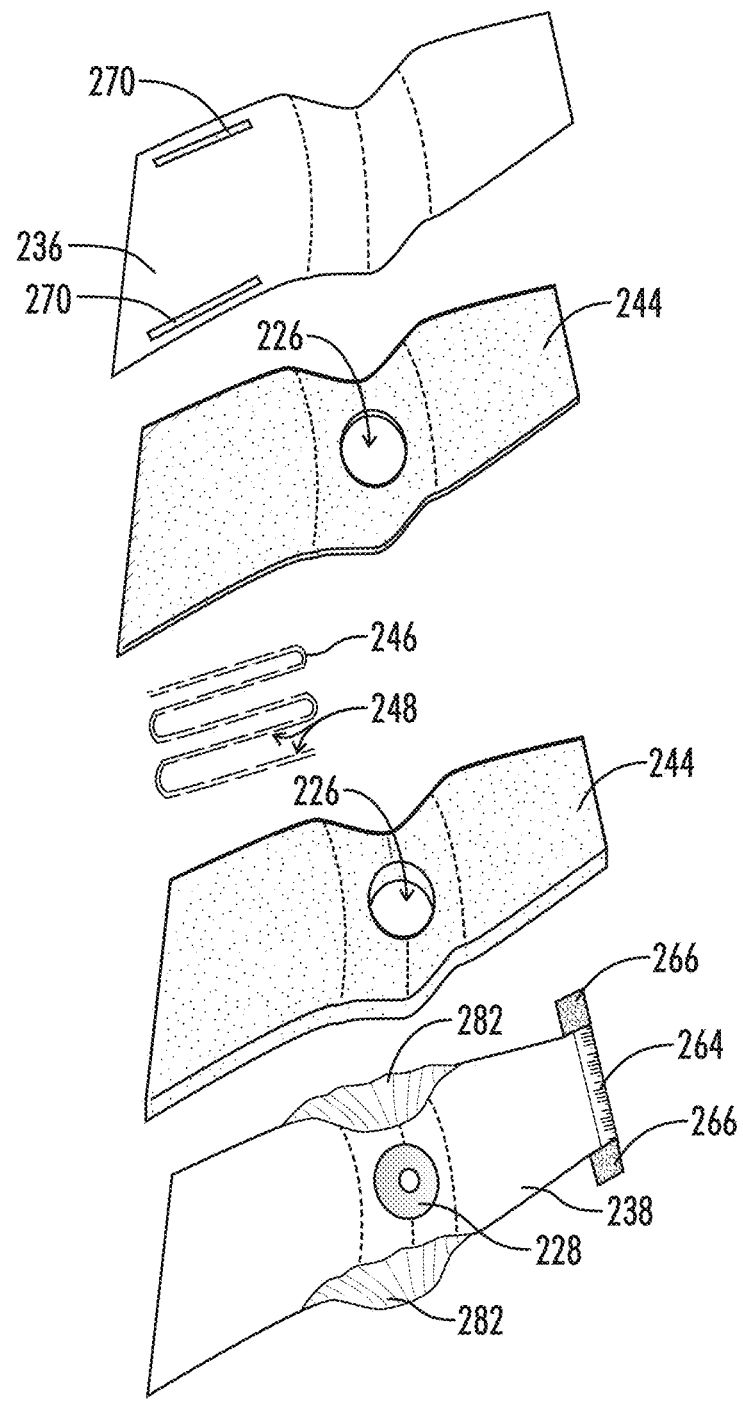
FIG. 24 is an exploded perspective view of the incontinence aid of FIG. 23.
Figure 25:
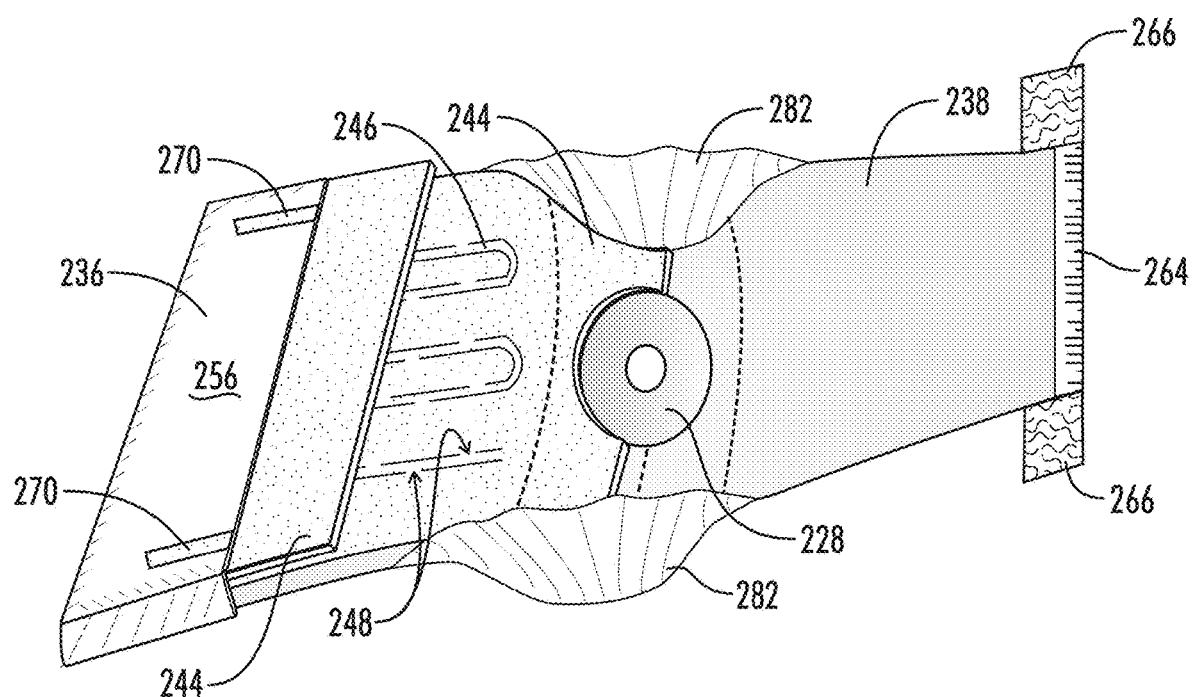
FIG. 25 is a perspective cutaway view of the incontinence aid of FIG. 23.
Figure 26:
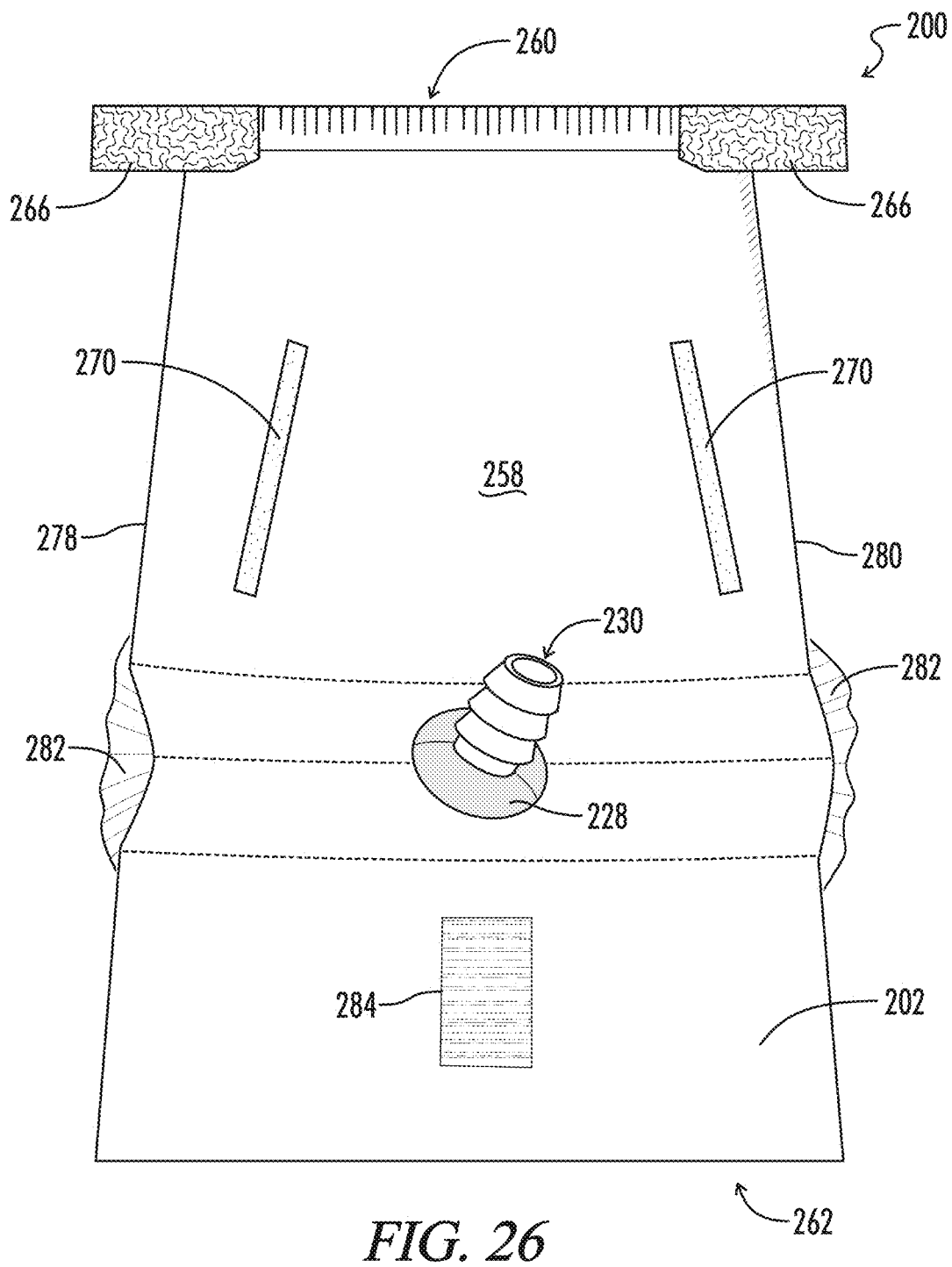
FIG. 26 is a rear elevation view of the incontinence aid of FIG. 23.
Figure 27:
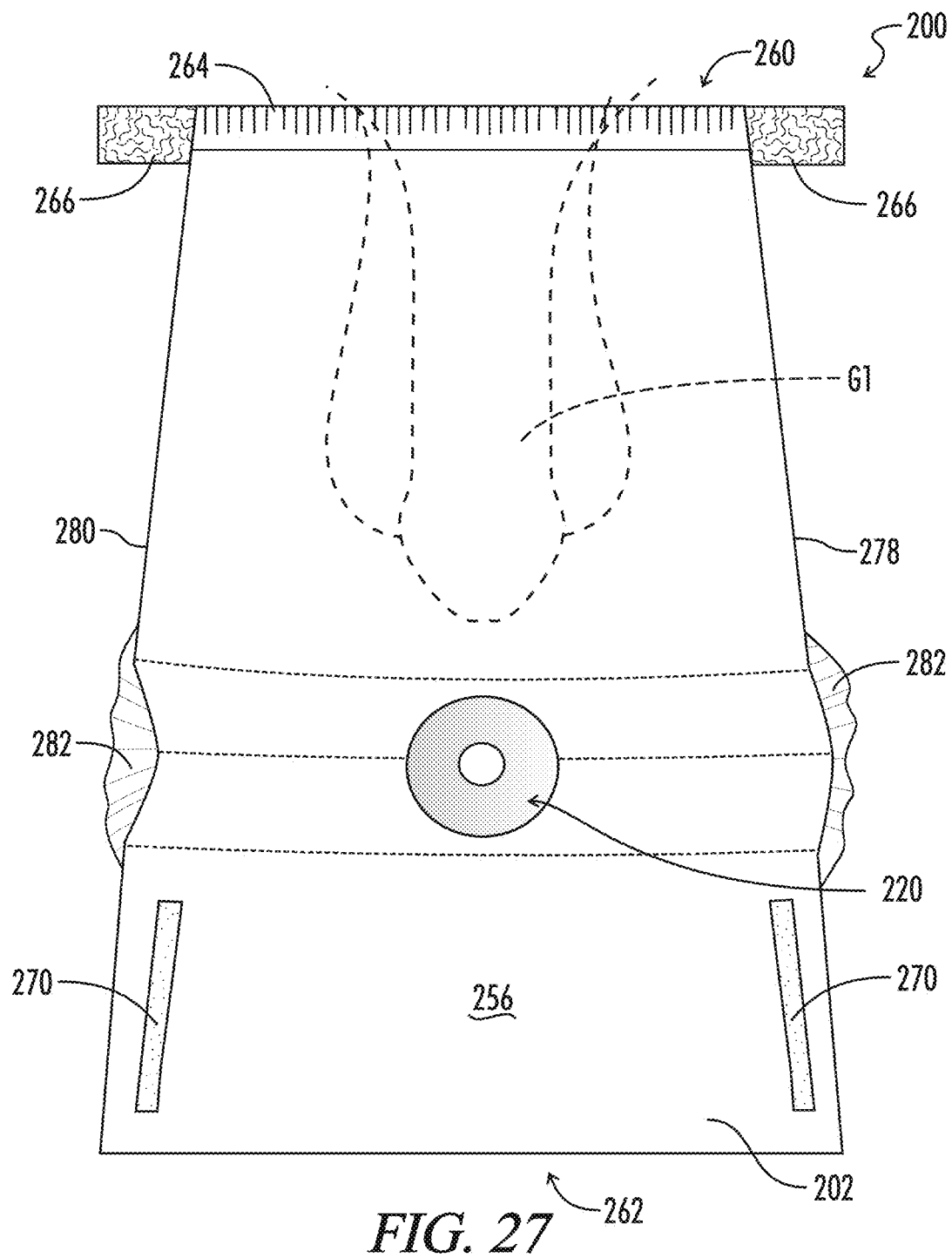
FIG. 27 is a front elevation view of the incontinence aid of FIG. 23 in position to be attached to the user.
Figure 28:
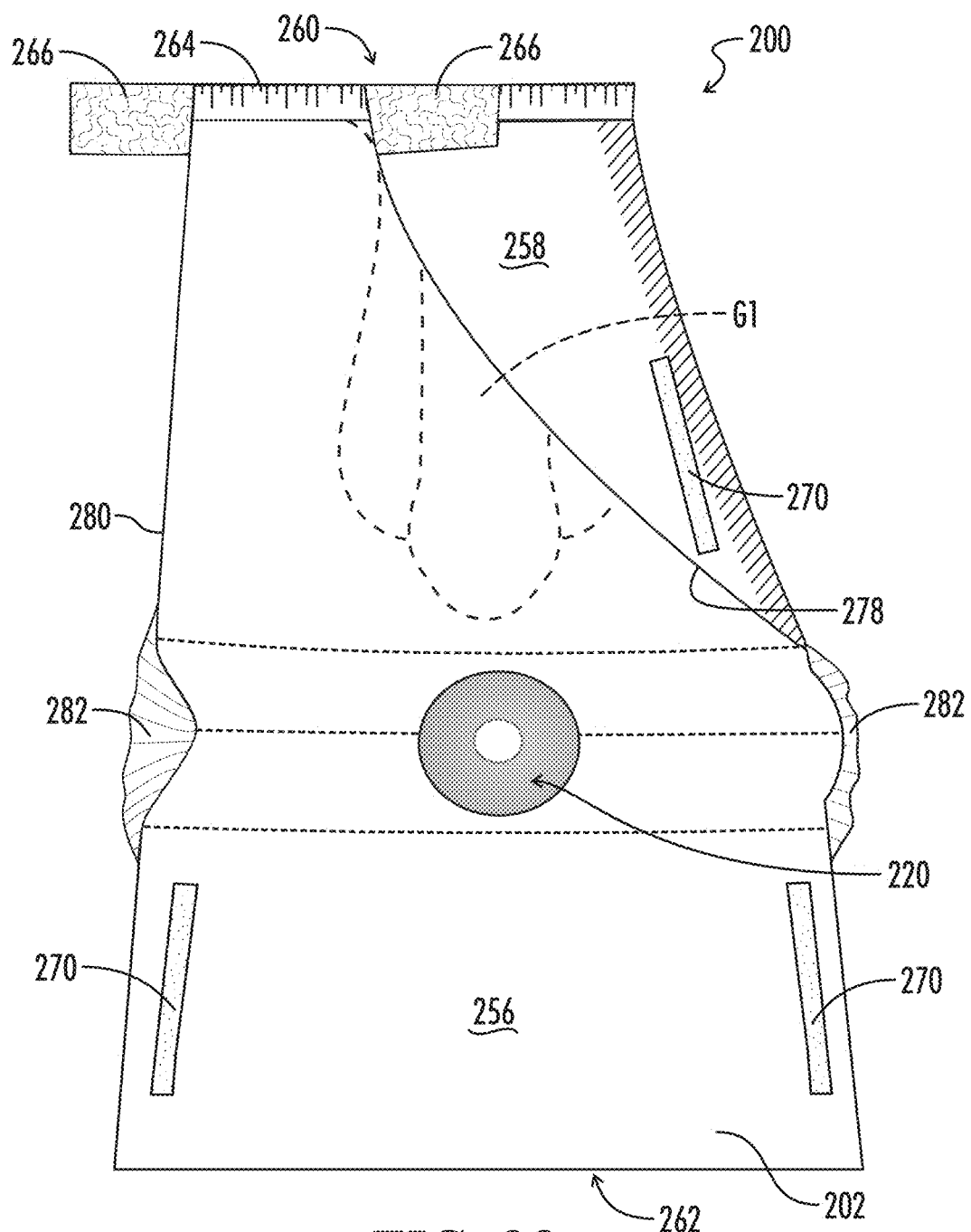
FIG. 28 is a front elevation view of the incontinence aid of FIG. 23 in a subsequent step of attachment to the user.
Figure 29:
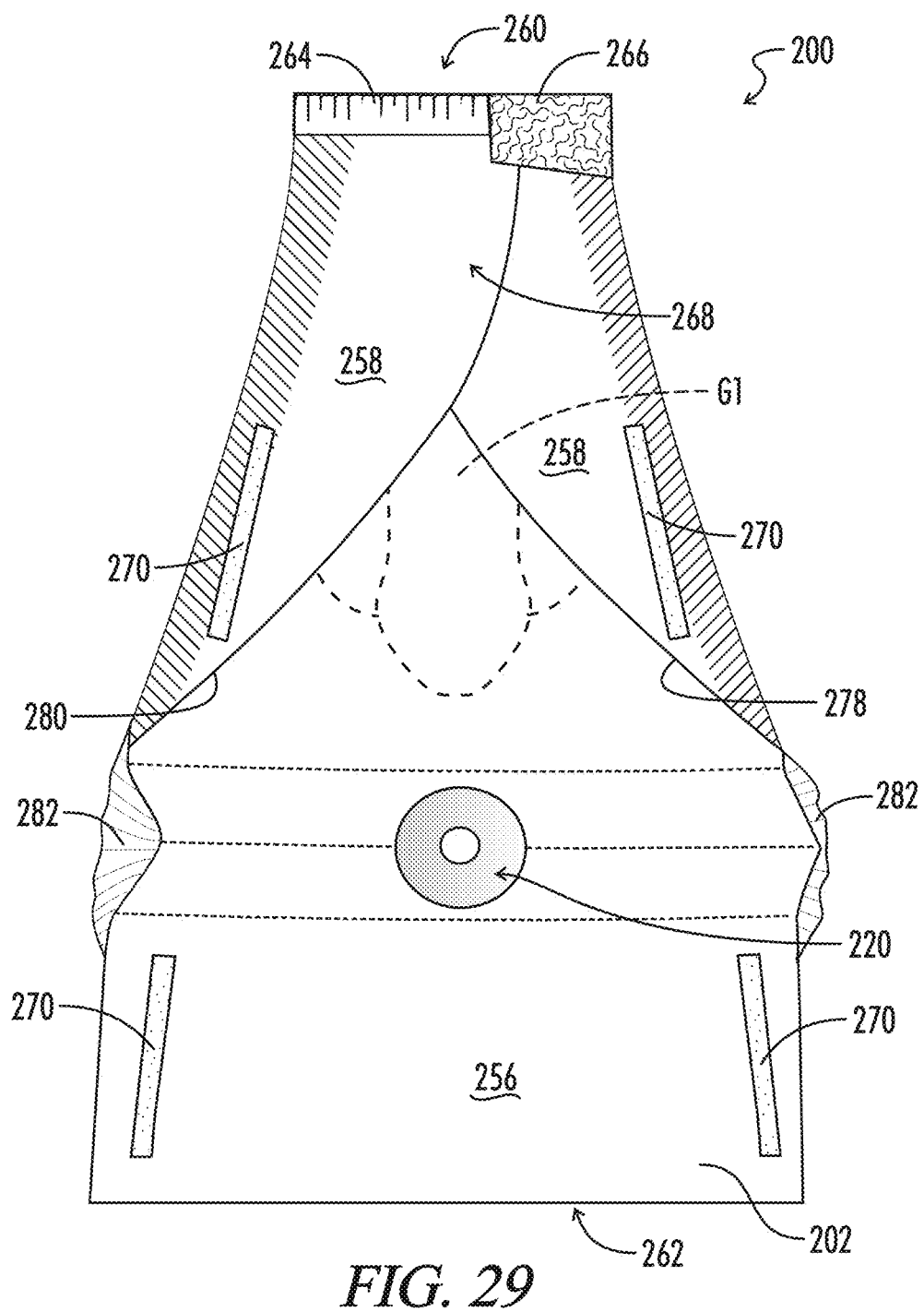
FIG. 29 is a front elevation view of the incontinence aid of FIG. 23 in a further subsequent step of attachment to the user.
Figure 30:
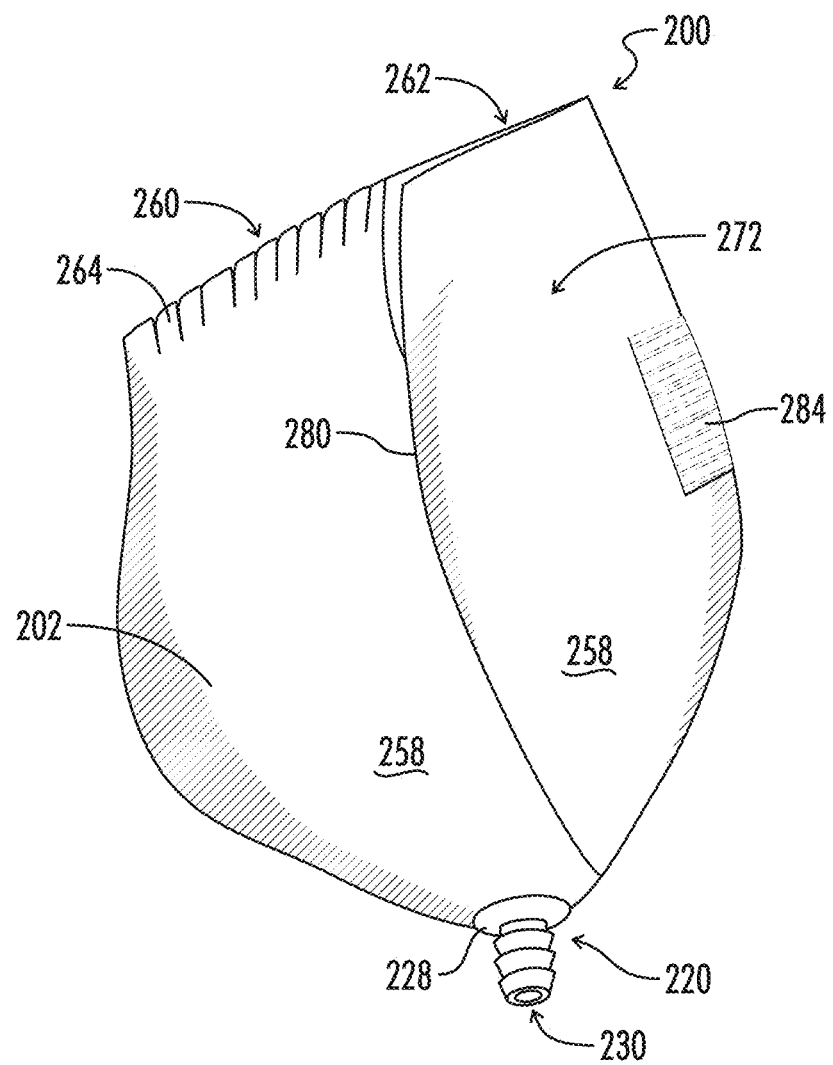
FIG. 30 is a side elevation view of the incontinence aid of FIG. 23 in a configuration to be attached to the user.

The incontinence aid 200, also as shown in FIGS. 17 and 18, may include one or more internal liquid passages 246 as described above. The liquid passage 246 may be disposed between a skin engagement layer 236 and a waterproof layer 238. In many embodiments, the liquid passage 246 may be disposed between absorbent layers 244.

Turning now to FIGS. 23-30, the incontinence aid 200 may further include a drain 220 as described above. The waterproof layer 238 may include a hole 240 defined therein. The absorbent layers 244 may also include a hole 226 defined therein as part of the drain 220.

As shown in FIGS. 8, 12, 13, 19, 26, and 30, the incontinence aid 200 may also include one or more exterior fasteners 284. The exterior fastener 284 may be positioned such that the incontinence aid 200 may removably connect to the user's undergarments during use. This connection may allow for additional support, helping to maintain the incontinence aid 200 in place even when containing considerable amounts of fluid. A further benefit of the exterior fastener 284 connecting to the user's undergarments may be that the design may allow for the user to pull away the second overlapping portion 272 of the pad body 202 by simply pulling down the user's undergarments. A user may then conveniently and quickly be able to use the restroom. After using the restroom, the user may then return the user's undergarments to the wearing position and may reengage the second fastener 270 to secure the second overlapping portion 272 of the pad body 202 in place.

This written description uses examples to disclose the invention and also to enable any person skilled in the art to practice the invention, including making and using any devices or systems. The patentable scope of the invention is defined by the claims, and may include other examples that occur to those skilled in the art. Such other examples are intended to be within the scope of the claims if they have structural elements that do not differ from the literal language of the claims or if they include equivalent structural elements with insubstantial differences from the literal language of the claims.

Although embodiments of the disclosure have been described using specific terms, such description is for illustrative purposes only. The words used are words of description rather than limitation. It is to be understood that changes and variations may be made by those of ordinary skill in the art without departing from the spirit or the scope of the present disclosure, which is set forth in the following claims. In addition, it should be understood that aspects of the various embodiments may be interchanged in whole or in part. While specific uses for the subject matter of the disclosure have been exemplified, other uses are contemplated. Therefore, the spirit and scope of the appended claims should not be limited to the description of the versions contained herein.

What is claimed is:

1. An incontinence aid for men, the incontinence aid comprising:
  a pad body including:
    an interior side,
    an exterior side opposite the interior side,
    a proximal end,
    a distal end opposite the proximal end, and
    a liquid receiving area;
  a first fastener permanently connected to the pad body adjacent the proximal end of the pad body, the first fastener configured to removably attach a first overlapping portion of the pad body adjacent the proximal end of the pad body to the exterior side of the pad body adjacent the proximal end of the pad body;
  a second fastener permanently connected to the pad body nearer the distal end of the pad body than the first fastener, the second fastener configured to removably attach a second overlapping portion of the pad body adjacent the distal end of the pad body to the exterior side of the pad body; and
  a liquid passage connected to the pad body, the liquid passage forming a boundary about a majority of the liquid receiving area, the liquid passage including at least one lateral opening facing the liquid receiving area.

2. The incontinence aid of claim 1, further comprising:
  a drain connected to the pad body, the drain configured to receive liquid from at least one of the liquid receiving area and the liquid passage.

3. The incontinence aid of claim 2, wherein:
  the drain is connected to the liquid receiving area of the pad body.

4. The incontinence aid of claim 3, further comprising:
  tubing in fluid communication with the drain.

5. The incontinence aid of claim 4, wherein:
  a liquid retention vessel remote from the pad body, the liquid retention vessel in fluid communication with the drain.

6. The incontinence aid of claim 2, wherein:
  the liquid passage further includes a first liquid passage open end and a second liquid passage open end; and
  the drain is connected to the pad body between the first liquid passage open end and the second liquid passage open end.

7. The incontinence aid of claim 2, wherein:
  the liquid receiving area includes a liquid collection reservoir defined in the pad body.

8. The incontinence aid of claim 7, wherein:
  the liquid collection reservoir includes a first thickness of the pad body;
  other portions of the pad body include a second thickness; and
  the second thickness is greater than the first thickness.

9. The incontinence aid of claim 8, wherein:
  the pad body further includes at least one ridge configured to direct liquid to the liquid collection reservoir;
  the at least one ridge includes a third thickness of the pad body; and
  the third thickness is greater than the first thickness and the second thickness.

10. The incontinence aid of claim 1, wherein:
  the liquid passage includes a water-proof material.

11. The incontinence aid of claim 1, wherein:
  the liquid passage is disposed between a skin engagement layer and a waterproof layer.

12. The incontinence aid of claim 1, wherein:
  the liquid passage is disposed between absorbent layers.

* * * * *